United States Patent [19]

Baracchini et al.

[11] Patent Number: 5,801,154
[45] Date of Patent: *Sep. 1, 1998

[54] ANTISENSE OLIGONUCLEOTIDE MODULATION OF MULTIDRUG RESISTANCE-ASSOCIATED PROTEIN

[75] Inventors: Edgardo Baracchini, San Diego; C. Frank Bennett, Carlsbad; Nicholas M. Dean, Encinitas, all of Calif.

[73] Assignee: Isis Pharmaceuticals, Inc., Carlsbad, Calif.

[*] Notice: The term of this patent shall not extend beyond the expiration date of Pat. No. 5,510,239.

[21] Appl. No.: 835,770

[22] Filed: Apr. 8, 1997

Related U.S. Application Data

[63] Continuation-in-part of Ser. No. 628,731, Apr. 16, 1996, which is a continuation-in-part of Ser. No. 136,811, Oct. 18, 1993, Pat. No. 5,510,239.

[51] Int. Cl.$^6$ ............... C12N 15/85; A61K 48/00; C12Q 1/68; C07H 21/04
[52] U.S. Cl. .............. 514/44; 435/6; 435/91.1; 435/171.3; 435/32.5; 536/23.1; 536/24.3; 536/24.5
[58] Field of Search ............... 435/6, 91.1, 320.1, 435/325, 366; 536/23.1, 24.5, 24.3; 514/44

[56] References Cited

U.S. PATENT DOCUMENTS

| | | | |
|---|---|---|---|
| 5,034,506 | 7/1991 | Summerton et al. | 528/391 |
| 5,138,045 | 8/1992 | Cook et al. | 536/23.1 |
| 5,218,105 | 6/1993 | Cook et al. | 536/25.31 |
| 5,459,255 | 10/1995 | Cook et al. | 536/27.13 |

FOREIGN PATENT DOCUMENTS

94/26764  11/1994  WIPO.

OTHER PUBLICATIONS

Canitrot et al., "MRP-associated multidrug resistance its reversal by 2'-modified antisense oligonucleotides", *Anti-Cancer Drugs* 1996, 7(suppl. 3), 93–99.
Cole et al., "Rapid chemosensitivity testing of human long tumor cells using the MTT assay", *Cancer Chemother. Pharmacol.* 1986, 17, 259–263.
Cole et al., "Overexpression of a Transporter Gene in Multidrug-Resistant Human Lung Cancer Cell Line", *Science* 1992, 258, 1650–1654.
Cole et al., "Multidrug Resistance–Associated Protein: Sequence Correction", *Science* 1993, 260, 879.
Crooke et al., "Pharmacokinetic Properties of Several Novel Oligonucleotide Analogs in mice", *J. Pharmacol. Exp. Ther.* 1996, 277, 923–937.
De Mesmaeker et al., "Antisense Oligonucleotides", *Acc. Chem. Res.* 1995, 28, 366–374.
Gao et al., "Reconstitution of ATP–dependent Leukotriene $C^4$ Tranport by Co-expression of Both Half-molecules of Human Multidrug Resistance Protein in Insect Cells", *J. Biol. Chem.* 1996, 271, 27782–27787.

Gebeyehu et al., "Novel biotinylated nucleotide—analogs for labeling and colorimetric detection of DNA", *Nucl. Acids Res.* 1987, 15,4513–4534.
Henderson, W.R., Jr., "The Role of Leukotrienes in Inflammation", *Ann. Int. Med.* 1994, 121, 684–697.
Kabanov et al., "A new class of antivirals: antisense oligonucleotides combined with a hydrophobic substituent effectively inhibit influenza virus reproduction and synthesis of virus–specific proteins in MDCK cells", *FEBS Lett.* 1990, 259, 327–330.
Kornberg, A., "Uncommon Nucleotides", *DNA Replication*, W.H. Freeman & Co., San Francisco, 1980, pp. 75–77.
Letsinger et al., "Cholesteryl–conjugated oligonucleotides: Synthesis, properties, and activity as inhibitors of replication of human immunodeficiency virus in cell culture", *Proc. Natl. Acad. Sci. USA* 1989, 86, 6553–6556.
Manoharan et al., "Cholic Acid–Oligonucleotides Conjugates for Antisense Applications", *Bioorg. Med. Chem. Let.* 1994, 4, 1053–1060.
Manoharan et al., "Chemical Modifications to Improve Uptake and Bioavailability of Antisense Oligonucleotides", *Ann. N.Y. Acad. Sci.* 1992, 660, 306–309.
Manoharan et al., "Introduction of a Lipophilic Thioether Tether in the Minor Groove of Nucleic Acids for Antisense Applications", *Bioorg. Med. Chem. Let.* 1993, 3, 2765–2770.
Manoharan et al., "Oligonucleotides Conjugates: Alteration of the Pharmacokinetic Properties of Antisense Agents", *Nucleosides & Nucleotides* 1995, 14, 969–973.
Manoharan et al., "Lipidic Nucleic Acids", *Tetrahedron Lett.* 1995, 36, 3651–3654.
1993 Catalog of Products for DNA Research, Glen Research, Sterling, VA, p. 21.
Martin, P., "Ein neuer Zugang zu 2'–O–Alkylribonucleosiden und Eigenschaften deren Oligonucleotides", *Helv. Chim. Acta* 1995, 78,486–504.
Mirski et al., "Multidrug Resistance in Human Small Cell Lung Cancer Cell Line Selected in Adriamycin", *Cancer Res.* 1987, 47, 2594–2598.
Mirski et al., "Antigens Associated with Multidrug Resistance in H69AR, a Small Cell Lung Cancer Cell Line", *Cancer Res.* 1989, 49, 5719–5724.

(List continued on next page.)

Primary Examiner—John L. LeGuyader
Attorney, Agent, or Firm—Law Offices of Jane Massey Licata

[57] ABSTRACT

Compositions and methods are provided for the treatment and diagnosis of diseases or conditions amenable to treatment through modulation of the synthesis or metabolism of multidrug resistance-associated protein (MRP). In accordance with referred embodiments, oligonucleotides are provided which are specifically hybridizable with nucleic acids encoding MRP. In a preferred embodiment, the oligonucleotide has at least one 2'-methoxyethoxy modification. Methods of preventing the development of multidrug resistance and of improving the efficacy of chemotherapy are also disclosed.

35 Claims, 11 Drawing Sheets

OTHER PUBLICATIONS

Mishra et al., "Improved leishmanicidal effect of phosphorothioate antisense oligonucleotides by LDL–mediated delivery", *Biochim. Biophys. Acta* 1995, 1264, 229–237.

Neilsen et al. "Sequence–Selective Recognition of DNA by Strand Displacement with a Thymine–Substituted Polyamide", *Science* 1991, 254, 1497–1500.

Oberhauser et al., "Effective incorporate of 2'–O–methyl–oligoribonucleotides into liposomes and enhanced cell associated through modification with thiocholesterol", *Nucl. Acids. Res.* 1992, 20, 533–538.

Sambrook et al., *Molecular Cloning. A Laboratory Manual*, Cold Spring Harbor Laboratory Press, 1989, vol. 2, pp. 10.59–10.61.

Sambrook et al., *"Molecular Cloning. A Laboratory Manual,"* Cold Spring Harbor Laboratory Press, 1989, vol. 2, pp. 11.31–11.32.

Saison–Behmoaras et al., "Short modified antisense oligonucleotides directed against Ha–ras point mutation induce selective cleavage of the mRNA and inhibit T24 cells proliferation", *EMBO J.* 1991, 10, 1111–1118.

Sanghvi, Y.S., in *Antisense Research and Applications*, Crooke and Lebleu, eds., CRC Press, Boca Raton, 1993, pp. 273–288.

Shea et al., "Synthesis, hybridization properties and antiviral activity of lipid–oligodeoxynucleotide conjugates", *Nucl. Acids Res.* 1990, 18, 3777–3783.

Slovak et al., "Localization of Novel Multidrug Resistance––associated Gene in the HT1080/DR4 and H69AR Human Tumor Cell Lines", *Cancer Res.* 1993, 53, 3221–3225.

Svinarchuk et al., "Inhibition of HIV proliferation in MT–4 cells by antisense oligonucleotide conjugated to lipophilic groups", *Biochimie* 1993, 75, 49–54.

Thierry et al., "Overcoming Multidrug Resistance in Human Tumor Cells Using Free and Liposomally Encapsulated Antisense Oilgodeoxynucleotides", *Biochem. Biophys. Res. Comm.* 1993, 190, 652–960.

Vasanthakumar, G. and N.K. Ahmed, "Modulation of Drug Resistance in a Daunorubicin Rsistant Subline with Oligonucleoside Methylphosphonates", *Cancer Commun.* 1989, 1, 225–232.

ANTISENSE OLIGONUCLEOTIDE MODULATION OF MULTIDRUG RESISTANCE-ASSOCIATED PROTEIN

RELATED APPLICATIONS

This application is a continuation-in-part of U.S. patent application Ser. No. 08/628,731, filed and U.S. patent application Ser. No. 08/136,811, filed Oct. 18, 1993, now issued as U.S. Pat. No. 5,510,239.

FIELD OF THE INVENTION

This invention relates to diagnostics, research reagents and therapies for multidrug resistance and for disease states which respond to modulation of the phenomenon of multidrug resistance. In particular, this invention relates to antisense oligonucleotide interactions with certain messenger ribonucleic acids (mRNAs) or DNAs involved in the synthesis of the multidrug resistance-associated protein (MRP). Antisense oligonucleotides designed to hybridize to the mRNA encoding MRP are provided. These oligonucleotides have been found to lead to the modulation of the activity of the RNA or DNA, and thus to the modulation of the synthesis and metabolism of MRP. Palliation and therapeutic effect result. These oligonucleotides can also be used in assays and diagnostics, and can be useful in distinguishing MRP-associated multidrug resistance from other multidrug resistance pathways.

BACKGROUND OF THE INVENTION

Acquired resistance to chemotherapy is a major problem in treatment of cancer by conventional cytotoxic drugs. Tumors may initially respond well to chemotherapy but later become resistant to a variety of unrelated drugs, leading to relapse. Multidrug resistance can arise via one of several independent pathways, any or all of which may be amenable to inhibition. One cause of multidrug resistance is believed to be overexpression of a transmembrane transport protein known as P-glycoprotein or MDR protein. Another distinct cause of multidrug resistance is believed to be overexpression of a member of the ATP-binding cassette transmembrane transporter superfamily known as multidrug resistance-associated protein (MRP). This protein is overexpressed in certain tumor cell lines which are multidrug resistant but do not overexpress P-glycoprotein. Cole et al. *Science* 1992, 258, 1650–1654; Slovak et al. *Cancer Res.* 1993, 53, 3221–3225. The gene encoding MRP was initially isolated from a multidrug-resistant small-cell lung cancer cell line. Small-cell lung cancer accounts for 20–25% of all lung cancer. Up to 90% of small-cell lung cancers respond initially to chemotherapy, but nearly all become multidrug resistant, leading to relapse.

MRP, unlike P-glycoprotein, has been shown to be a primary active ATP-dependent transporter of leukotrienes and other conjugated organic anions. Gao et al. *J. Biol. Chem.* 1996, 271, 27782–27787.

Compositions and methods for modulating and detecting MRP are the subject of this invention. Agents capable of reversing the phenomenon of multidrug resistance and thus "sensitizing" the drug resistant tumors to chemotherapy are desired. Cyclosporin A and other agents are able to reverse doxorubicin resistance in cells which overexpress MDR, but clinical use of these compounds is limited by their cytotoxicity. Further, these reversing agents do not work in cells which overexpress MRP. Antisense oligonucleotides targeted to the MDR mRNA encoding P-glycoprotein have been used to inhibit the synthesis of P-glycoprotein (MDR protein) and to partially reverse the multidrug resistance phenotype. Thierry et al. *Biochem. Biophys. Res. Comm.* 1993, 190, 952–960; Vasanthakumar, G. and N. K. Ahmed *Cancer Commun.* 1989, 1, 225–232.

While compositions and methods for reversing P-glycoprotein (MDR)-associated multidrug resistance or MDR synthesis have shown limited success, these are not targeted to the same target as the compositions and methods of the present invention. Consequently there remains a long-felt need for compositions and methods for modulation and diagnosis of other types of multidrug resistance. Oligonucleotides that are specifically hybridizable with MRP mRNA are desired for their diagnostic and therapeutic utility. Interference with MRP expression is desired as a means of reversing the multidrug resistance phenomenon, and making a distinction between multidrug resistance due to MRP and that due to other causes. Interference with MRP expression is also desired for improving the efficacy of conventional methods of cancer chemotherapy, particularly of lung cancer, most particularly of small-cell lung cancer.

Compositions and methods for treating inflammatory conditions are also desired. The role of leukotrienes in inflammatory conditions, particularly asthma, inflammatory bowel disease, rheumatoid arthritis and psoriasis, is well known and leukotriene inhibitors and antagonists are being examined as drugs. Henderson, W. R., Jr., *Ann. Int. Med.* 1994, 121, 684–697. Leukotriene release has also been implicated in other inflammatory conditions including allergic rhinitis, cystic fibrosis, adult respiratory distress syndrome, and glomerulonephritis. Because MRP functions as a primary ATP-dependent transporter of cysteinyl leukotrienes, compositions and methods for modulating MRP expression are believed to have therapeutic utility for these and other inflammatory conditions in which leukotriene release is involved.

BRIEF DESCRIPTION OF THE DRAWINGS

FIG. 5 is a line graph showing the suppression of MRP protein levels after treatment with antisense oligonucleotides.

SUMMARY OF THE INVENTION

Figure 1A:
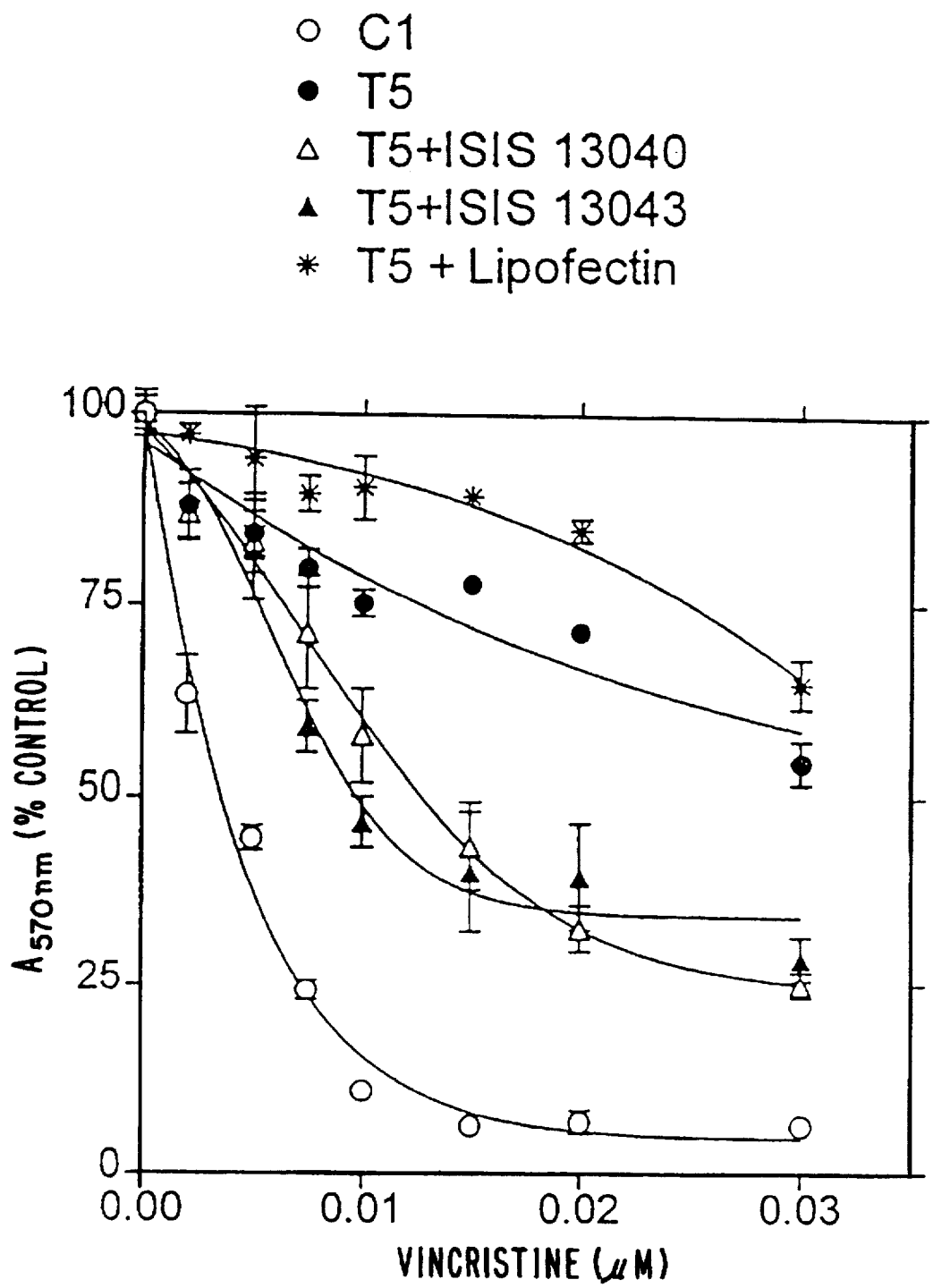
FIGS. 1a and 1b are line drawings showing the reversal of resistance of HeLa T5 cells to vincristine (FIG. 1a) or doxorubicin (FIG. 1b) (escalating doses along the abscissa) after treatment with ISIS 13040 or its scrambled control, ISIS 13043. Open circles=C1 control cells; solid circles= untreated T5 cells; open triangles=T5 cells+ISIS 13040; closed triangles=T5 cells+ISIS 13043; asterisks= LIPOFECTIN™ alone.
Figure 1B:
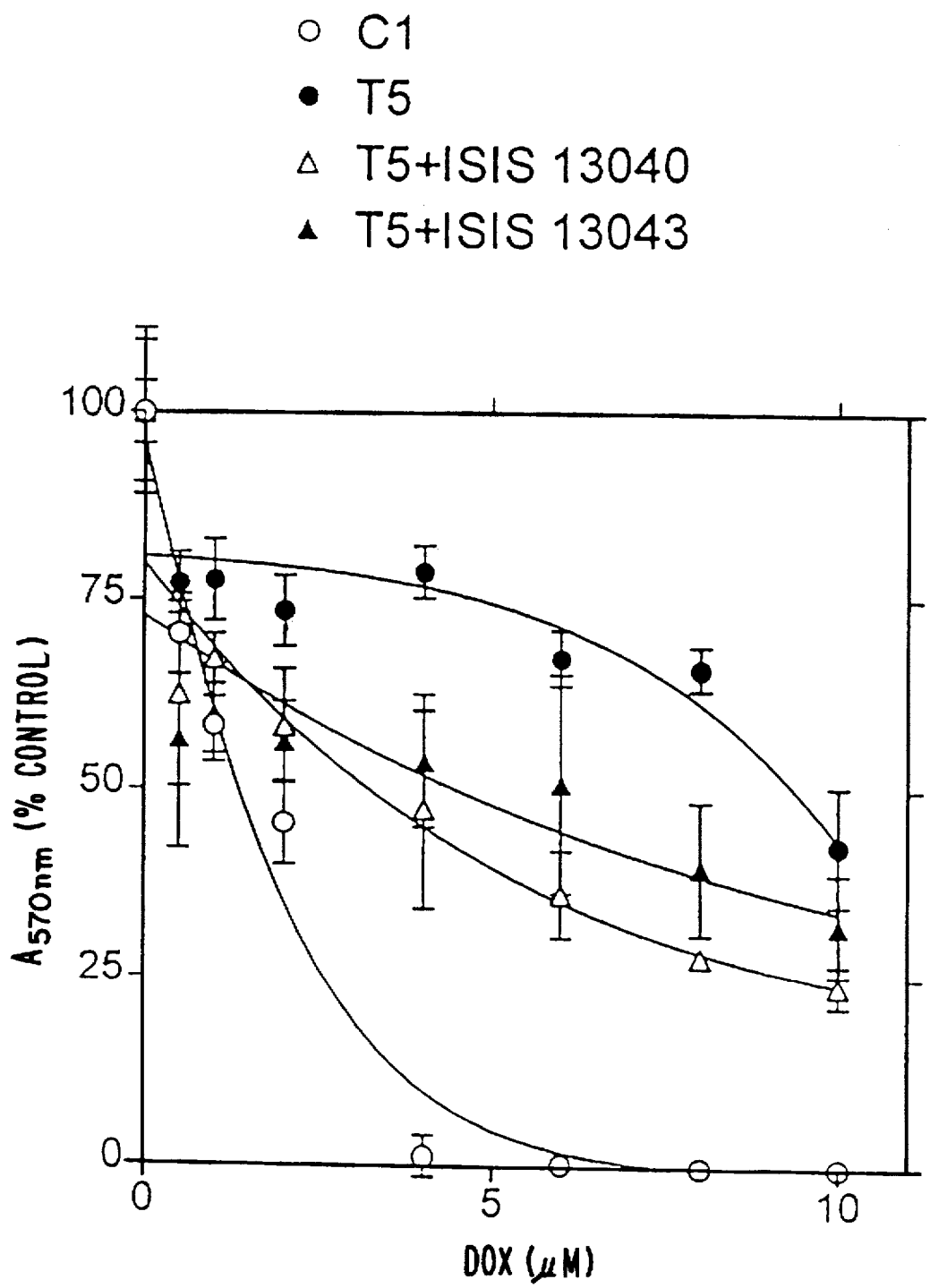

In accordance with the present invention, oligonucleotides are provided which specifically hybridize with nucleic acids encoding multidrug resistance-associated protein (MRP). The oligonucleotides are designed to bind either directly to mRNA or to a selected DNA portion forming a triple stranded structure, thereby modulating the amount of mRNA made from the gene. In either case, expression of MRP protein is ultimately modulated. "Hybridization," in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which are known to form two hydrogen bonds between them. "Specifically hybridizable" indicates a sufficient degree of complementarity to avoid non-specific binding of the oligonucleotide to non-target sequences. It is well known in the art that an oligonucleotide need not be 100% complementary to its target nucleic acid sequence to be specifically hybridizable.

The relationship between an oligonucleotide and its complementary target nucleic acid is commonly denoted as "antisense". In the context of the present invention, the "target" is a nucleic acid encoding multi-drug resistance-associated protein (MRP); in other words, the MRP gene or mRNA expressed from the MRP gene.

It is preferred to target specific genes for antisense attack. It has been discovered that the gene coding for MRP is particularly useful for this approach. Inhibition of MRP expression is expected to be useful for the treatment of multidrug resistance. However, "modulation" in the context of this invention means either an increase or decrease (stimulation or inhibition) of MRP expression.

Methods of modulating the synthesis of MRP in cells and tissues comprising contacting an animal suspected of having multidrug-resistant cells or tissues with an oligonucleotide specifically hybridizable with nucleic acids encoding the MRP protein are provided.

Methods of treating an animal suspected of having a condition characterized by elevated levels of MRP are also provided. Such methods comprise administering to an animal a therapeutically effective amount of an oligonucleotide specifically hybridizable with nucleic acids encoding the MRP protein.

Other aspects of the invention are directed to methods for improving the efficacy of chemotherapy and preventing the development of multidrug resistance during chemotherapeutic drug treatment of a disease. Such methods comprise administering to an animal an appropriate amount of oligonucleotide specifically hybridizable with nucleic acids encoding the MRP protein in conjunction with a chemotherapeutic drug treatment.

Methods for diagnosis are also a part of this invention, and include methods for determining MRP-associated multidrug resistance as being distinct from other pathways of multidrug resistance development. Such methods comprise contacting cells or tissues or bodily fluids from the diseased animals with oligonucleotides in accordance with this invention in order to detect MRP overexpression.

DETAILED DESCRIPTION OF PREFERRED EMBODIMENTS

Oligonucleotides have recently become accepted as drugs for the treatment of disease states in animals and man. For example, workers in the field have now identified antisense, triplex and other oligonucleotide therapeutic compositions which are capable of modulating expression of genes implicated in viral, fungal and metabolic diseases. Numerous antisense oligonucleotide drugs have been safely administered to humans and a number of clinical trials are presently underway. Efficacy has been demonstrated for several oligonucleotide drugs, directed to both viral and cellular gene targets. It is thus established that oligonucleotides can be useful therapeutics.

For therapeutics, an animal suspected of having a disease which can be treated by decreasing the expression of MRP is treated by administering oligonucleotides in accordance with this invention. Oligonucleotides may be formulated in a pharmaceutical composition, which may include carriers, thickeners, diluents, buffers, preservatives, surface active agents, liposomes or lipid formulations and the like in addition to the oligonucleotide. Pharmaceutical compositions may also include one or more active ingredients such as antimicrobial agents, antiinflammatory agents, anesthetics, and the like in addition to oligonucleotide. Oligonucleotides may be administered in conjunction with conventional cancer chemotherapeutic drugs which are well known to those skilled in the art.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, pulmonary administration, e.g., by inhalation or insufflation, or intrathecal or intraventricular administration. Oligonucleotides with at least one 2'-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may also be included.

Compositions for parenteral, intrathecal or intraventricular administration may include sterile aqueous solutions which may also contain buffers, diluents and other suitable additives.

The formulation of therapeutic compositions and their subsequent administration is within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or even once every 2 to 20 years. Persons of ordinary skill in the art can easily determine repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

The present invention is also suitable for detection of MRP overexpression in tissue or other samples from patients who have developed multidrug resistance. A number of assays may be formulated employing the present invention, which assays will commonly comprise contacting a tissue sample with an oligonucleotide of the invention under conditions selected to permit detection, and usually quantitation, of such inhibition. For example, radiolabelled oligonucleotides can be prepared by $^{32}$P labeling at the 5' end with polynucleotide kinase. Sambrook et al., *Molecular Cloning. A Laboratory Manual*, Cold Spring Harbor Laboratory Press, 1989, Volume 2, pg. 10.59. Radiolabeled oligonucleotides are then contacted with tissue or cell samples suspected of MRP overexpression or with RNA extracted from such samples. The sample is then washed to remove unbound oligonucleotide. Radioactivity remaining in the sample indicates bound oligonucleotide (which in turn indicates expression of the nucleic acids encoding MRP) and can be quantitated using a scintillation counter or other routine means. Comparison to appropriate controls allows overexpression of MRP to be determined. Radiolabeled oligonucleotide can also be used to perform autoradiography of tissues to determine the localization, distribution and quantitation of MRP overexpression for research, diagnostic and therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing MRP. Quantitation of the silver grains permits MRP overexpression to be detected.

Analogous assays for fluorescent detection of MRP expression can be developed using oligonucleotides of the invention which are conjugated with fluorescein or other fluorescent tag instead of radiolabeling. Such conjugations are routinely accomplished during solid phase synthesis using fluorescently-labeled amidites or CPG (e.g., fluorescein-labeled amidites or CPG available from Glen Research, Sterling, Va. See 1993 Catalog of Products for DNA Research, Glen Research, Sterling, Va., pg. 21).

Each of these assay formats is known in the art. One of skill could easily adapt these known assays for detection of MRP expression in accordance with the teachings of the invention providing a novel and useful means to detect MRP expression.

In addition, the ability of the oligonucleotides of the present invention to inhibit MRP synthesis in cultured diseased cells is extremely useful in distinguishing drug resistance which is MRP-associated from that which arises via another pathway. In case of a disease state such as cancer, oligonucleotide-treated cells from the drug resistant tumor sites can be cultured and screened for reversal of drug resistance, i.e., increased sensitivity to chemotherapeutic drugs as quantitated by a decrease in the $IC_{50}$ values. This information can be used to treat the disease state more efficaciously.

The oligonucleotides of this invention may also be used for research purposes. Thus, the specific hybridization exhibited by the oligonucleotides may be used for assays, purifications, cellular product preparations and in other methodologies which would be appreciated by persons of ordinary skill in the art.

The present invention employs oligonucleotides for use in antisense inhibition of the function of RNA and DNA encoding multidrug resistance-associated protein (MRP). In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. A discussion of antisense oligonucleotides and some desirable modifications can be found in De Mesmaeker et al., *Acc. Chem. Res.* 1995, 28, 366–374.

Specific examples of some preferred oligonucleotides envisioned for this invention include those containing modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, $CH_2$—N($CH_3$)—O—$CH_2$ [known as a methylene (methylimino) or MMI backbone], $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—P—O—$CH_2$. The amide backbones disclosed by De Mesmaeker et al. (*Acc. Chem. Res.* 1995, 28, 366–374) are also preferred. Also preferred are oligonucleotides having morpholino backbone structures (Summerton and Weller, U.S. Pat. No. 5,034,506). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al., *Science* 1991, 254, 1497).

Oligonucleotides may also contain one or more substituted sugar moieties. Preferred oligonucleotides comprise one of the following at the 2' position: OH, SH, $SCH_3$, F, OCN, $OCH_3OCH_3$, $OCH_3O(CH_2)_nCH_3$, $O(CH_2)_nNH_2$ or $O(CH_2)_nCH_3$ where n is from 1 to about 10; $C_1$ to $C_{10}$ lower alkyl, alkoxyalkoxy, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O-CH$_2$CH$_2$OCH$_3$, also known as 2'-O-(2-methoxyethyl)] (Martin et al., *Helv. Chim. Acta* 1995, 78, 486). Other preferred modifications include 2'-methoxy (2'-O-CH$_3$), 2'-propoxy (2'-OCH$_2$CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-me pyrimidines, particularly 5-methylcytosine (also referred to as 5-methyl-2'deoxycytosine and often referred to in the art as 5-me-C), 5-hydroxymethylcytosine (HMC), glycosyl HMC and gentobiosyl HMC, as well as synthetic nucleobases, e.g., 2-aminoadenine, 2-thiouracil, 2-thiothymine, 5-bromouracil, 5-hydroxymethyluracil, 8-azaguanine, 7-deazaguanine, N$^6$(6-aminohexyl)adenine and 2,6-diaminopurine. Kornberg, A., *DNA Replication*, W. H. Freeman & Co., San Francisco, 1980, pp 75–77; Gebeyehu, G., et al. *Nucl. Acids Res.* 1987, 15,4513). A "universal" base known in the art, e.g., inosine, may be included. 5-me-C substitutions have been shown to increase nucleic acid duplex stability by 0.6°–1.2° C. (Sanghvi, Y. S., in *Antisense Research and Applications*, Crooke and Lebleu, eds., CRC Press, Boca Raton, 1993, pp. 276–278) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al. *Proc. Natl. Acad. Sci. USA* 1989, 86, 6553), cholic acid (Manoharan et al. *Bioorg. Med. Chem. Let.* 1994, 4, 1053), a thioether, e.g., hexyl-S-tritylthiol (Manoharan et al. *Ann. N.Y. Acad. Sci.* 1992, 660, 306; Manoharan et al. *Bioorg. Med. Chem. Let.* 1993, 3, 2765), a thiocholesterol (Oberhauser et al. *Nucl. Acids Res.* 1992, 20, 533), an aliphatic chain, e.g., dodecandiol or undecyl residues (Saison-Behmoaras et al. *EMBO J.* 1991, 10, 111; Kabanov et al. *FEBS Lett.* 1990, 259, 327; Svinarchuk et al. *Biochimie* 1993, 75, 49), a phospholipid, e.g., di-hexadecyl-rac-glycerol or triethylammonium 1,2-di-O-hexadecyl-rac-glycero-3-H-phosphonate (Manoharan et al. *Tetrahedron Lett.* 1995, 36, 3651; Shea et al. *Nucl. Acids Res.* 1990, 18, 3777), a polyamine or a polyethylene glycol chain (Manoharan et al. *Nucleosides & Nucleotides* 1995, 14, 969), or adamantine acetic acid (Manoharan et al. *Tetrahedron Lett.* 1995, 36, 3651), a palmityl moiety (Mishra et al. *Biochim. Biophys. Acta* 1995, 1264, 229), or an octadecylamine or hexylamino-carbonyl-oxycholesterol moiety (Crooke et al. *J. Pharmacol. Exp. Ther.* 1996, 277, 923). Oligonucleotides comprising lipophilic moieties, and methods for preparing such oligonucleotides are known in the art, for example, U.S. Pat. Nos. 5,138,045, 5,218,105 and 5,459,255.

The oligonucleotides of the invention may be provided as prodrugs, which comprise one or more moieties which are cleaved off, generally in the body, to yield an active oligonucleotide. One example of a prodrug approach is described by Imbach et al. in WO Publication 94/26764.

It is not necessary for all positions in a given oligonucleotide to be uniformly modified and, in fact, more than one of the aforementioned modifications may be incorporated in a single oligonucleotide or even within a single nucleoside within an oligonucleotide. The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Consequently, comparable results can often be obtained with shorter oligonucleotides when chimeric oligos are used, compared to phosphorothioate deoxyoligonucleotides hybridizing to the same target region. Cleavage of the RNA target can be routinely detected by gel electrophoresis and, if necessary, associated nucleic acid hybridization techniques known in the art. Typically, chimeric oligonucleotides are "gapped" oligonucleotides (or "gapmers") in which a region of deoxynucleotides (the "gap"), preferably containing at least four contiguous deoxynucleotides, is flanked by regions of modified nucleotides, preferably 2'-sugar modified nucleotides. In a preferred embodiment, the flanking regions (or "wings") contain 2'-alkoxy or 2'alkoxyalkoxy modifications, more preferably 2'-methoxyethoxy. In preferred embodiments the backbone may be phosphorothioate throughout or may be phosphodiester in the "wings" and phosphorothioate in the "gap". In other preferred embodiments, chimeric oligonucleotides may be "winged" oligonucleotides (or "wingmers" or hemichimeras) in which there is a deoxy "gap", preferably at least 4 contiguous deoxynucleotides, flanked on either the 5' or the 3' side by a region of modified nucleotides. Again, the flanking region (or "wing") preferably contains 2'-alkoxy or 2'alkoxyalkoxy modifications, more preferably 2'-methoxyethoxy and the backbone may be phosphorothioate throughout or may be phosphodiester in the "wing" and phosphorothioate in the "gap". Other configurations of chimeric oligonucleotide are also comprehended by this invention. These may involve other modifications of the sugar, base or backbone, preferably in the oligonucleotide wing(s).

The oligonucleotides in accordance with this invention preferably comprise from about 8 to about 30 nucleotides. It is more preferred that such oligonucleotides comprise from about 12 to 25 nucleotides. As will be appreciated, a nucleotide is a base-sugar combination suitably bound to an adjacent nucleotide through phosphodiester or other bonds.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; however, the actual synthesis of the oligonucleotides is well within the talents of the routineer. It is also known to use similar techniques to prepare other oligonucleotides such as the phosphorothioates and alkylated derivatives.

It is preferred to target specific genes for antisense attack. "Targeting" an oligonucleotide to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid from an infectious agent. In the present invention, the target is a nucleic acid encoding multidrug resistance-associated protein. The targeting process also includes determination of a site or sites within this gene for the oligonucleotide interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Because, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding MRP, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. The open reading frame (ORF) or "coding region", which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene) and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene). The transcription initiation site, or "5' cap site" and the 5' cap region (which encompasses from about 25 to about 50 contiguous nucleotides at the extreme 5' terminus of a capped mRNA) may also be effective targets. mRNA splice sites may also be preferred target regions, and are particularly useful in situations where aberrant splicing is implicated in disease, or where an overproduction of a particular mRNA splice product is implicated in disease. Where gene deletion rearrangements exist, aberrant fusion junctions are also preferred targets. Once the target site has been identified, oligonucleotides are chosen which are sufficiently complementary to the target, i.e., hybridize sufficiently well and with sufficient specificity, to give the desired effect under conditions in which specific hybridization is desired, i.e., under physiological conditions in the case of in vivo assays or therapeutic treatment or, in the case of in vitro methods, under conditions in which the methods are used. In preferred embodiments of the present invention, the oligonucleotides are specifically hybridizable with a transcription initiation site, a translation initiation site, coding sequences and sequences in the 5'- and 3'-untranslated regions of mRNA encoding MRP.

MRP belongs to the superfamily of ATP-binding cassette transport systems. This family includes the cystic fibrosis transmembrane conductance regulator, P-glycoprotein, and other transport proteins. The human MRP protein is 1531 amino acids in length and is encoded by an mRNA which is approximately 6.5 kb in length. Cole et al. *Science* 1992, 258, 1650-1654; Cole et al. *Science* 1993, 260, 879 (sequence correction); Slovak et al. *Cancer Res.* 1993, 53, 3221-3225. Antisense oligonucleotides (shown in Table 1) were designed to be specifically hybridizable with sequences in the 5'-untranslated region, 3'-untranslated region and coding region of the MRP gene. The sequence of the MRP gene is available in publications [Cole et al. *Science* 1992, 258, 1650-1654; Cole et al. *Science* 1993, 260, 879 (sequence correction)] or through Genbank accession number L05628.

TABLE 1

Antisense Oligonucleotides Specifically Hybridizable With MRP (All are phosphorothioates; ISIS 7607 is also 2'-O-methyl)

| ISIS # | TARGET REGION | SEQUENCE | SEQ ID NO: |
|---|---|---|---|
| 7607 | 5' UTR | CGG GGC CGC AAC GCC GCC UG | 1 |
| 7608 | 5' UTR | CGG GGC CGC AAC GCC GCC TG | 2 |
| 7606 | 5' UTR | GGT GAT CGG GCC CGG TTG CT | 3 |
| 7595 | 5' UTR | CCG GTG GCG CGG GCG GCG GC | 4 |
| 7592 | AUG | AGC CCC GGA GCG CCA TGC CG | 5 |
| 7593 | Coding | TCG GAG CCA TCG GCG CTG CA | 6 |
| 7594 | Coding | GGC ACC CAC ACG AGG ACC GT | 7 |
| 7597 | Coding | TGC TGT TCG TGC CCC CGC CG | 8 |
| 7598 | Coding | CGC GCT GCT TCT GGC CCC CA | 9 |
| 7599 | Coding | GCG GCG ATG GGC GTG GCC AG | 10 |
| 7600 | Coding | CAG GAG GTC CGA TGG GGC GC | 11 |
| 7601 | Coding | GCT CAC ACC AAG CCG GCG TC | 12 |
| 7603 | 3' UTR | AGG CCC TGC AGT TCT GAC CA | 13 |
| 7605 | 3' UTR | CTC CTC CCT GGG CGC TGG CA | 14 |
| 7602 | 3' UTR | ACC GGA TGG CGG TGG CTG CT | 15 |
| 7604 | 3' UTR | CGC ATC TCT GTC TCT CCT GG | 16 |

Preferred oligonucleotides useful in the invention comprise one of these sequences, or part thereof.

H69AR cells were treated with phosphorothioate oligonucleotides (SEQ ID NO: 1-16) in the presence of LIPO- FECTIN™ (GIBCO/BRL) as described in the following examples. Oligonucleotides ISIS 7597 and ISIS 7598 (SEQ ID NO: 8 and SEQ ID NO: 9), both specifically hybridizable to the coding region of MRP, consistently inhibited steady-state MRP protein levels by greater than 30% compared to LIPOFECTIN™ controls in multiple ELISA experiments. In one experiment, ISIS 7597 inhibited MRP protein levels by over 95%. Oligonucleotides ISIS 7597 and 7598 are therefore preferred. It should be noted that the ELISA assay measures steady-state levels of MRP protein; because of the long half-life of the MRP protein, complete inhibition of MRP protein synthesis would be expected to be reflected as a decrease, but not complete loss, of MRP protein in these assays. This level of inhibition in this assay is considered to be significant. In Northern blot analysis of the effects of ISIS 7597 and 7598 on MRP mRNA levels, both oligonucleotides were demonstrated to virtually eliminate MRP mRNA expression.

Based on results obtained with the oligonucleotides of Table 1, additional phosphorothioate oligonucleotides were designed. These oligonucleotides are shown in Table 2.

TABLE 2

Phosphorothioate Antisense Oligonucleotides Specifically Hybridizable With MRP

| ISIS # | TARGET REGION | SEQUENCE | SEQ ID NO: |
|---|---|---|---|
| 8356 | AUG | CAG AAG CCC CGG AGC GCC AT | 17 |
| 8358 | Coding | GCC CCC GCC GTC TTT GAC AG | 18 |
| 8359 | Coding | GTG ATG CTG TTC GTG CCC CC | 19 |
| 8357 | Coding | CTC ACG GTG ATG CTG TTC GT | 20 |
| 8362 | Coding | CCC CCA GAC AGG TTC ACG CC | 21 |
| 8361 | Coding | CTG GCC CCC AGA CAG GTT CA | 22 |
| 8360 | Coding | GCC AGG CTC ACG CGC TGC TT | 23 |
| 8363 | 3' UTR | CAC AGC CAG TTC CAG GCA GG | 24 |
| 8364 | 3' UTR | CCT GGG TCT TCA CAG CCA GT | 25 |

Chimeric oligonucleotides having SEQ ID NO: 8 were prepared. These oligonucleotides had uniform phosphorothioate backbones and central "gap" regions of 8 deoxynucleotides flanked by 2 regions of 2'-O-propyl modified nucleotides (ISIS 9659) or 2'-fluoro modified nucleotides (ISIS 9661).

Further, chimeric oligonucleotides having SEQ ID NO: 9 were prepared. These oligonucleotides had uniform phosphorothioate backbones and central "gap" regions of 8 deoxynucleotides flanked by 2 regions of 2'-O-propyl modified nucleotides (ISIS 9660) or 2'-fluoro modified nucleotides (ISIS 9662).

Additional oligonucleotides targeted to human MRP were synthesized. These are shown in Table 3. ISIS 9659, 9661, 11471, 11468 and 11469 have all been shown to inhibit MRP expression in a dose- and sequence-dependent manner. Canitrot et al. *Anti-Cancer Drugs* 1996, 7(suppl. 3), 93–99.

TABLE 3

Antisense Oligonucleotides Targeted to MRP

| ISIS # | TARGET REGION | SEQUENCE | MODIFICATION | SEQ ID NO: |
|---|---|---|---|---|
| 9567 | Coding | TGC TGT TCG TGC CCC CGC CG | PS/2'-F | 8 |
| 11468 | Coding | TGC TGT TCG TGC CCC CGC CG | PS/2'-F | 8 |
| 11469 | Coding | TGC TGT TCG TGC CCC CGC CG | PS/2'-F | 8 |
| 11584 | Coding | TGC TGT TCG TGC CCC CGC CG | PS/2'-F | 8 |
| 11585 | Coding | CGC GCT GCT TCT GGC CCC CA | PS/2'-F | 9 |
| 11586 | Coding | TGC TGT TCG TGC CCC CGC CG | PS/2'-F | 8 |
| 11471 | Coding | TGC TGT TCG TGC CCC CGC CG | PS/2'-O-propyl | 8 |
| 11077 | Coding | TGC TGT TCG TGC CCC CGC CG | PS/2'-O-hexylamino-cholesterol | 8 |
| 9658 | Sense | CGG CGG GGG CAC GAA CAG CA | PS | 26 |
| 12680 | Sense | CGG CGG GGG CAC GAA CAG CA | PS/2'-O-propyl | 26 |

TABLE 4

Antisense Oligonucleotides Targeted to MRP

| ISIS # | TARGET REGION | SEQUENCE | MODIFICATION | SEQ ID NO: |
|---|---|---|---|---|
| 13038 | Coding | TGC TGT TCG TGC CCC CGC CG | PO/PS/2'-MOE | 8 |
| 13039 | Coding | TGC TGT TCG TGC CCC CGC CG | PS/2'-MOE | 8 |
| 13040 | Coding | TGC TGT TCG TGC CCC CGC CG | PO/PS/2'-MOE | 8 |
| 13041 | Coding | TGC TGT TCG TGC CCC CGC CG | PS/2'-MOE | 8 |
| 15479 | Sense control | CGG CGG GGG CAC GAA CAG CA | PS/2'-MOE | 26 |
| 15480 | Sense control | CGG CGG GGG CAC GAA CAG CA | PS/2'-MOE | 26 |
| 13042 | Scrambled | TCG TGG CCG CGT TCT CCC CG | PS/2'-MOE | 27 |
| 13043 | Scrambled | TCG TGG CCG CGT TCT CCC CG | PO/PS/2'-MOE | 27 |
| 13044 | Scrambled | TCG TGG CCG CGT TCT CCC CG | PO/PS/2'-MOE | 27 |
| 13045 | Scrambled | TCG TGG CCG CGT TCT CCC CG | PS/2'-MOE | 27 |
| 15477 | Scrambled | CGT GTT GCT CGT GCC CGC CC | PS/2'-MOE | 28 |
| 15478 | Scrambled | CGT GTT GCT CGT GCC CGC CC | PS/2'-MOE | 28 |

Reversal of drug resistance in HeLa T5 cells following treatment with 2-methoxyethoxy antisense oligonucleotides T5 cells are drug-resistant transfected HeLa cells which express elevated levels of MRP. They were obtained by stable transfection with an MRP cDNA expression vector. C1 HeLa cells were transfected with the vector alone and serve as controls. Canitrot et al. *Anti-Cancer Drugs* 1996, 7 (suppl. 3), 93–99. T5 and C1 cells were treated with antisense oligonucleotide (500 nM in the presence of LIPOFECTIN™) as described in Canitrot et al., supra, except that cells were treated twice with oligonucleotide, on days 1 and 4 after plating, and then exposed to either vincristine or doxorubicin on day 5. The MTT assay for chemosensitivity was done on day 8.

The oligonucleotides tested were chimeric 2'-methoxyethoxy oligonucleotides: ISIS 13038 (mixed PS/PO backbone) and ISIS 13039 (PS backbone), each of which has a 12-deoxynucleotide gap; their scrambled controls, ISIS 13044 and 13045, respectively; ISIS 13040 (mixed PS/PO backbone) and ISIS 13041 (PS backbone), each of which has a 8-deoxynucleotide gap, and their scrambled controls, ISIS 13043 and 13042, respectively. As shown in Table 3, the 3'-most nucleotide of each of these oligonucleotides was a 2'-deoxynucleotide (for ease of synthesis). All were tested against both vincristine and doxorubicin.

The results of these experiments are shown in FIGS. 1–4. The absorbance at 570 nm (Y-axis) is a measure of the viable cells remaining, thus low absorbance reflects cytotoxicity caused by the chemotherapeutic agent, vincristine or doxorubicin. C1 cells are not MRP overexpressers and thus are not resistant to vincristine or doxorubicin and are killed (open circles). T5 cells overexpress MRP, are drug resistant and are resistant to vincristine (closed circles).

Figure 2A:
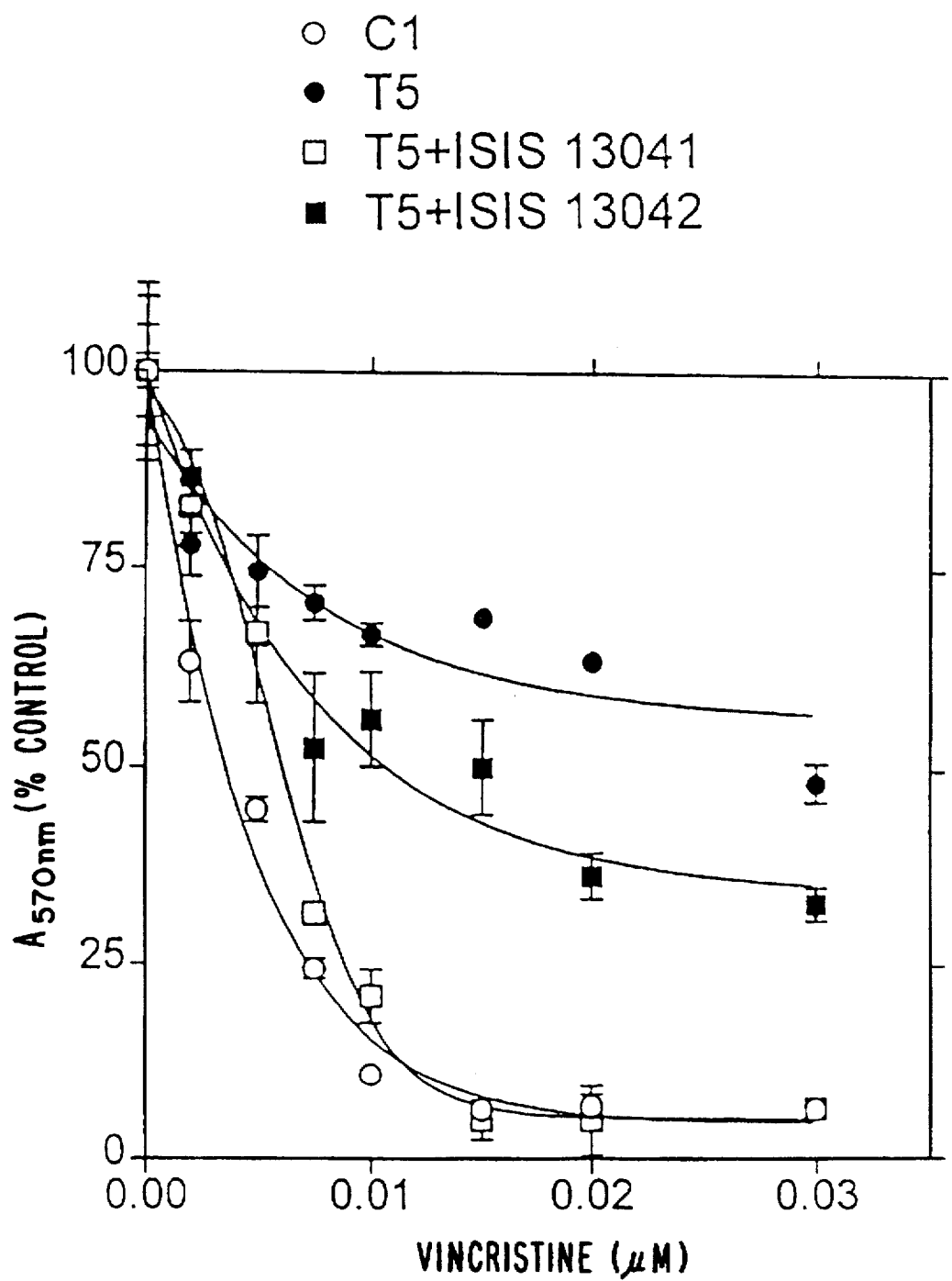
FIGS. 2a and 2b are line drawings showing the reversal of resistance of HeLa T5 cells to vincristine (FIG. 2a) or doxorubicin (FIG. 2b) (escalating doses along the abscissa) after treatment with ISIS 13041 or its scrambled control, ISIS 13042. Open circles=C1 control cells; solid circles= untreated T5 cells; open squares=T5 cells+ISIS 13041; closed squares=T5 cells+ISIS 13042.
Figure 2B:
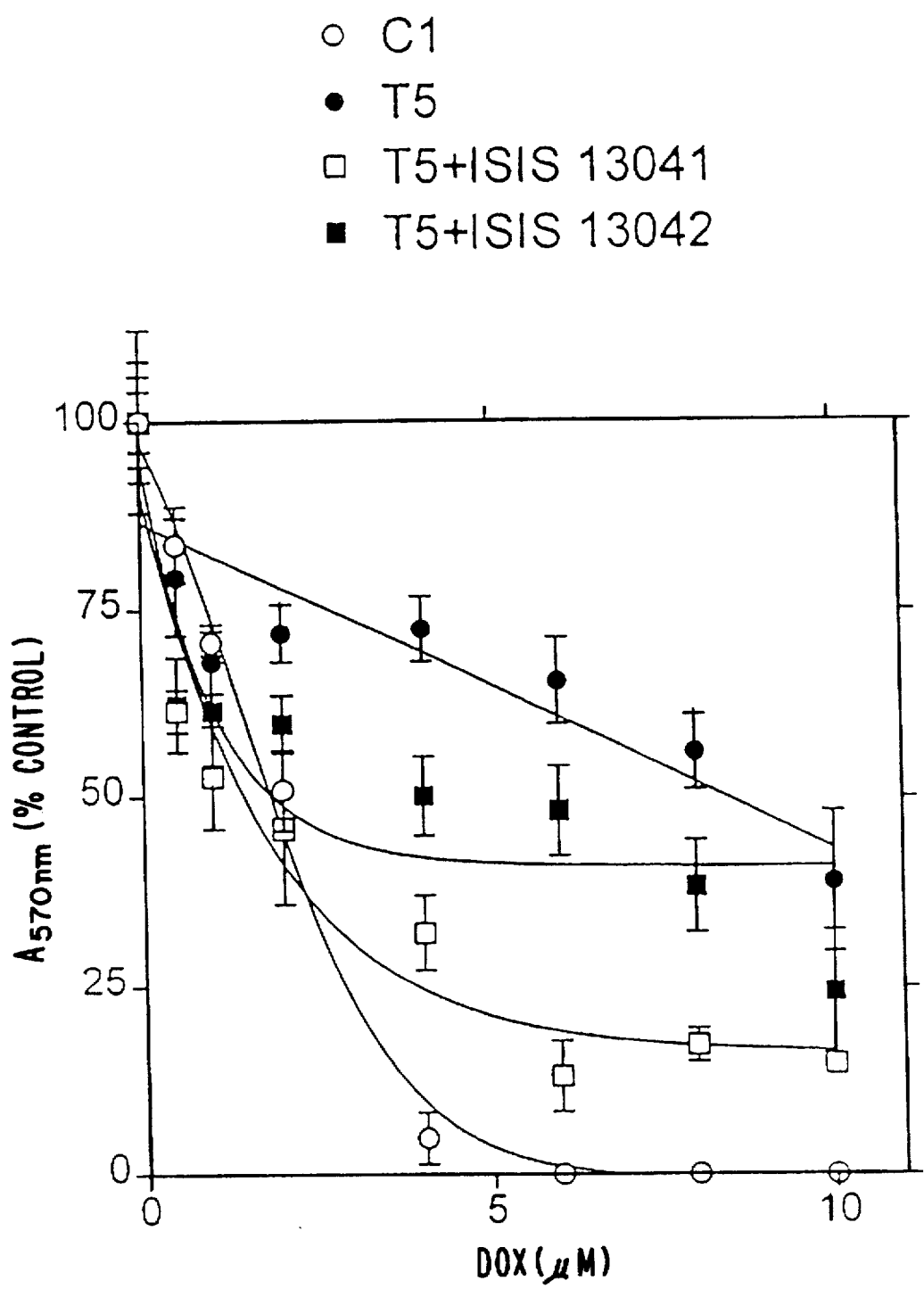
Figure 3A:
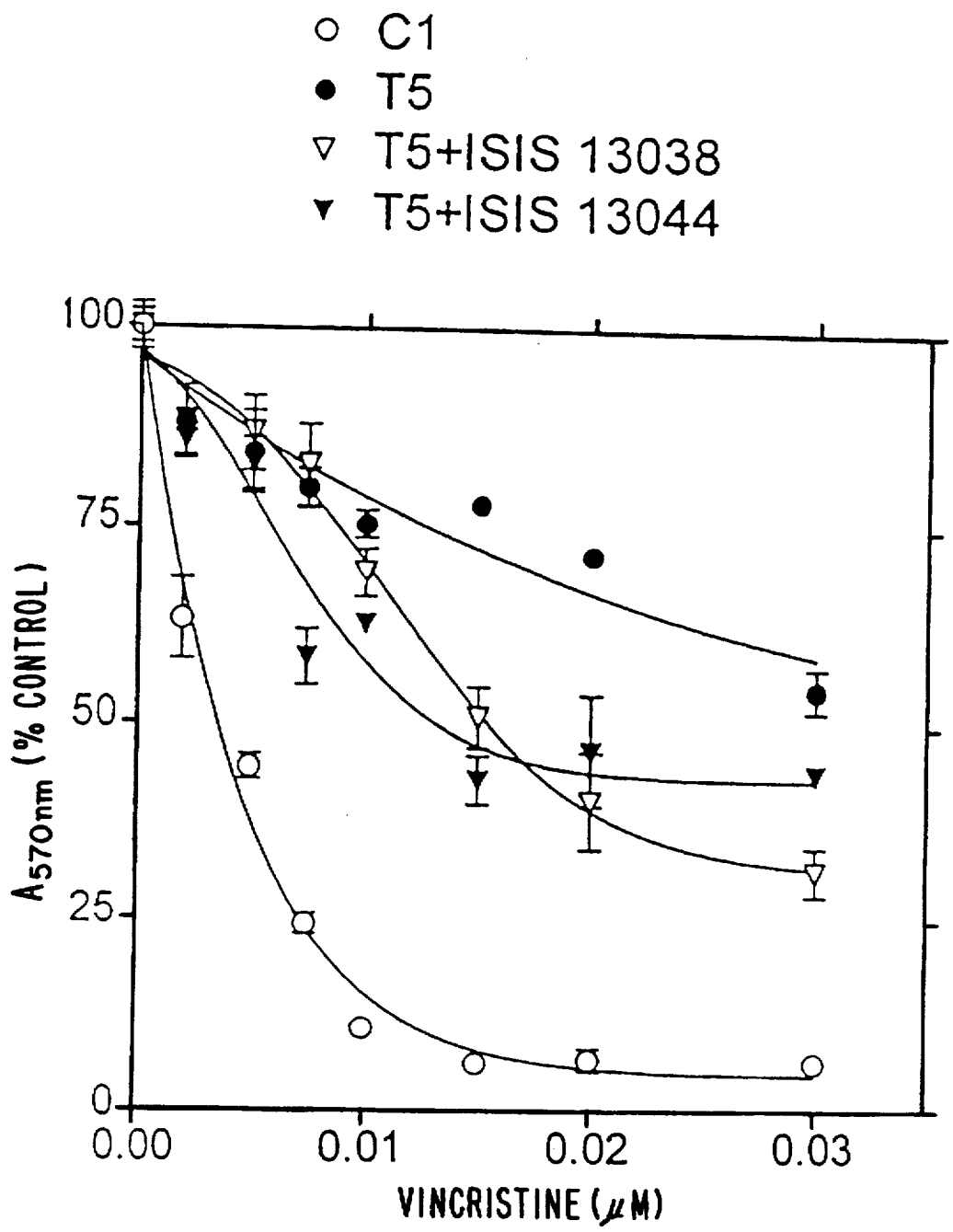
FIGS. 3a and 3b are line drawings showing the reversal of resistance of HeLa T5 cells to vincristine (FIG. 3a) or doxorubicin (FIG. 3b) (escalating doses along the abscissa) after treatment with ISIS 13038 or its scrambled control, ISIS 13044. Open circles=C1 control cells; solid circles= untreated T5 cells; open inverted triangles=T5 cells+ISIS 13038; closed inverted triangles=T5 cells+ISIS 13044.
Figure 3B:
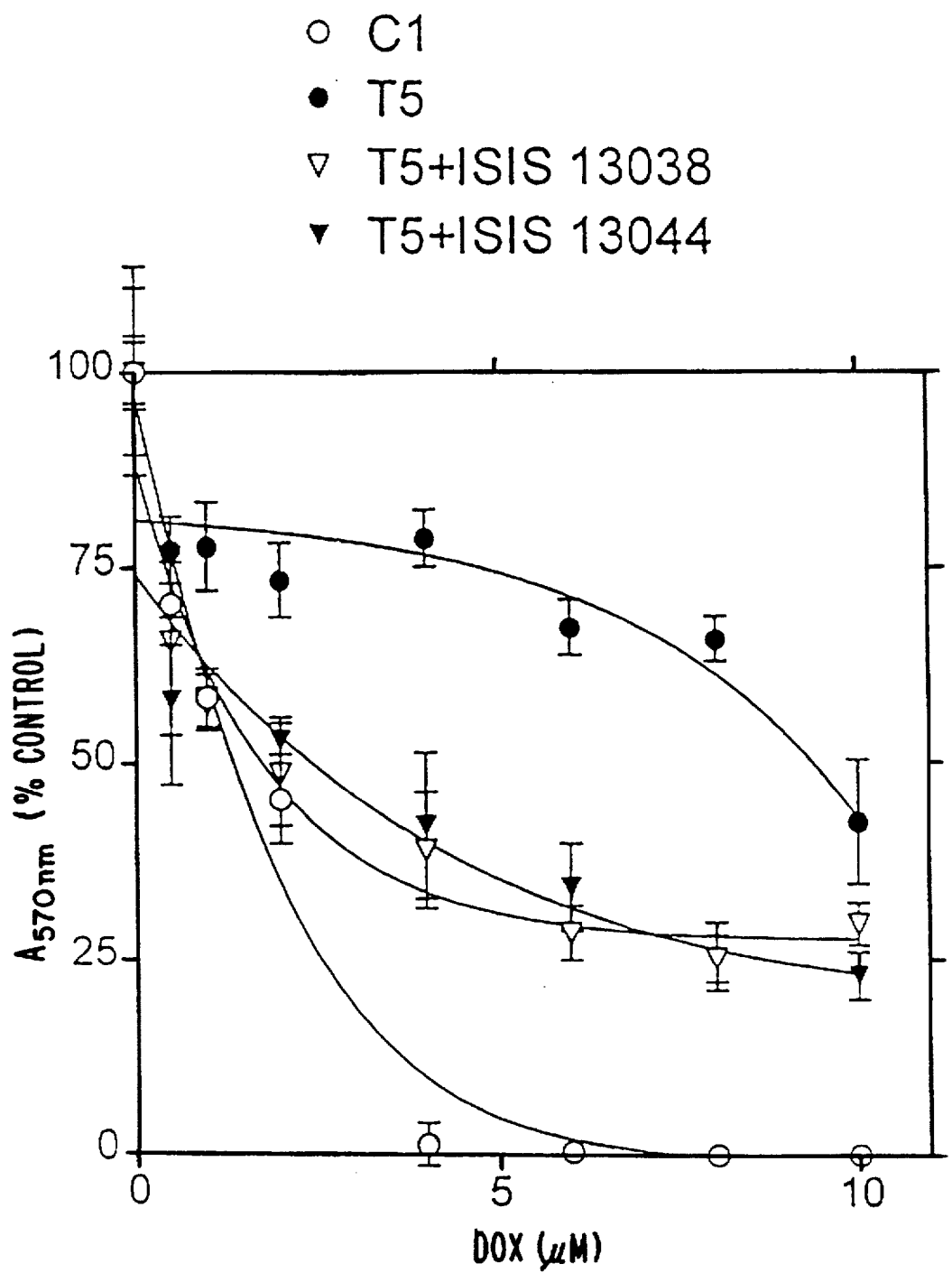
Figure 4A:
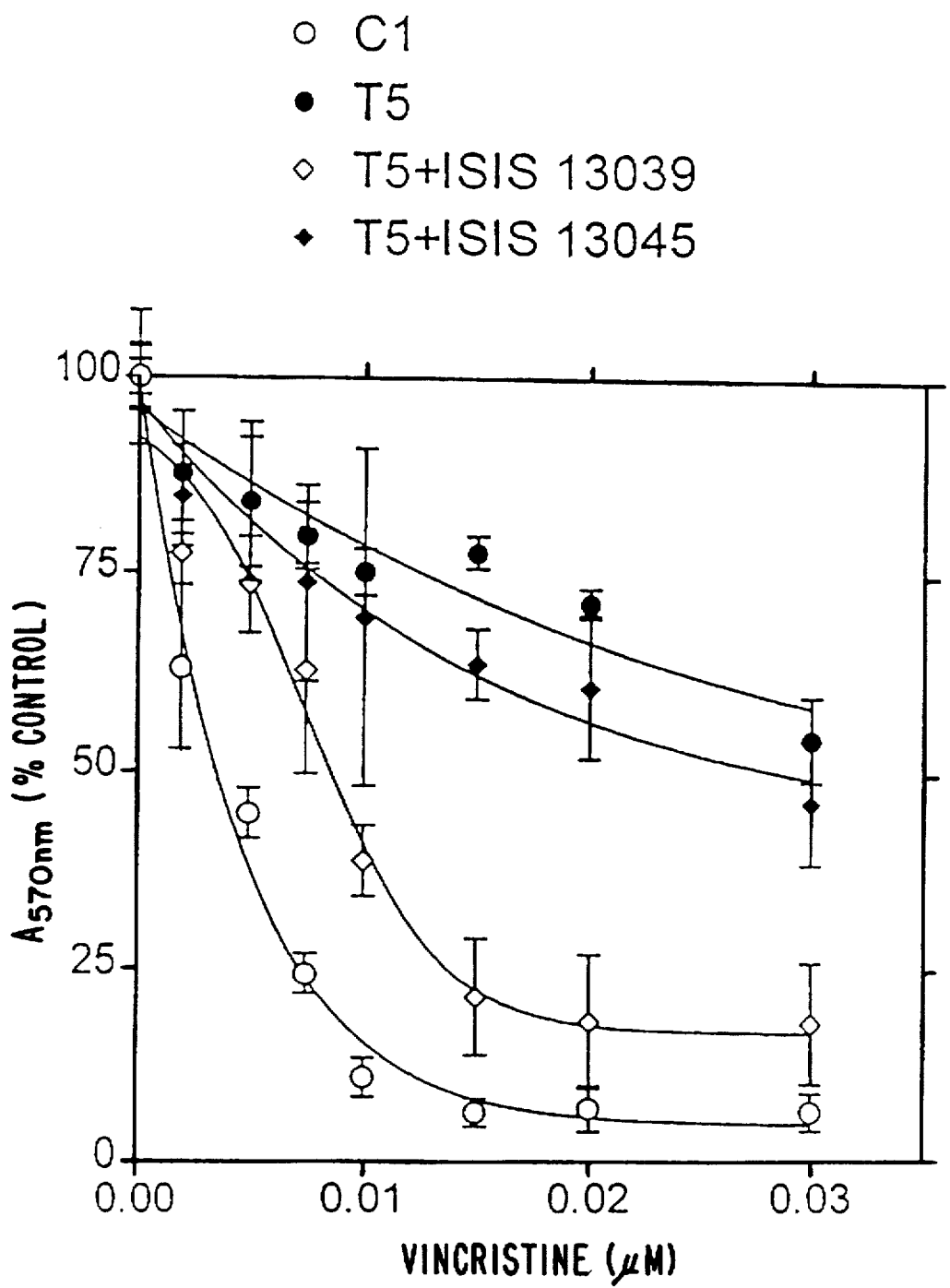
FIGS. 4a and 4b are line drawings showing the reversal of resistance of HeLa T5 cells to vincristine (FIG. 4a) or doxorubicin (FIG. 4b) (escalating doses along the abscissa) after treatment with ISIS 13039 or its scrambled control, ISIS 13045. Open circles=C1 control cells; solid circles= untreated T5 cells; open diamonds=T5 cells+ISIS 13039; closed diamonds=T5 cells+ISIS 13045.
Figure 4B:
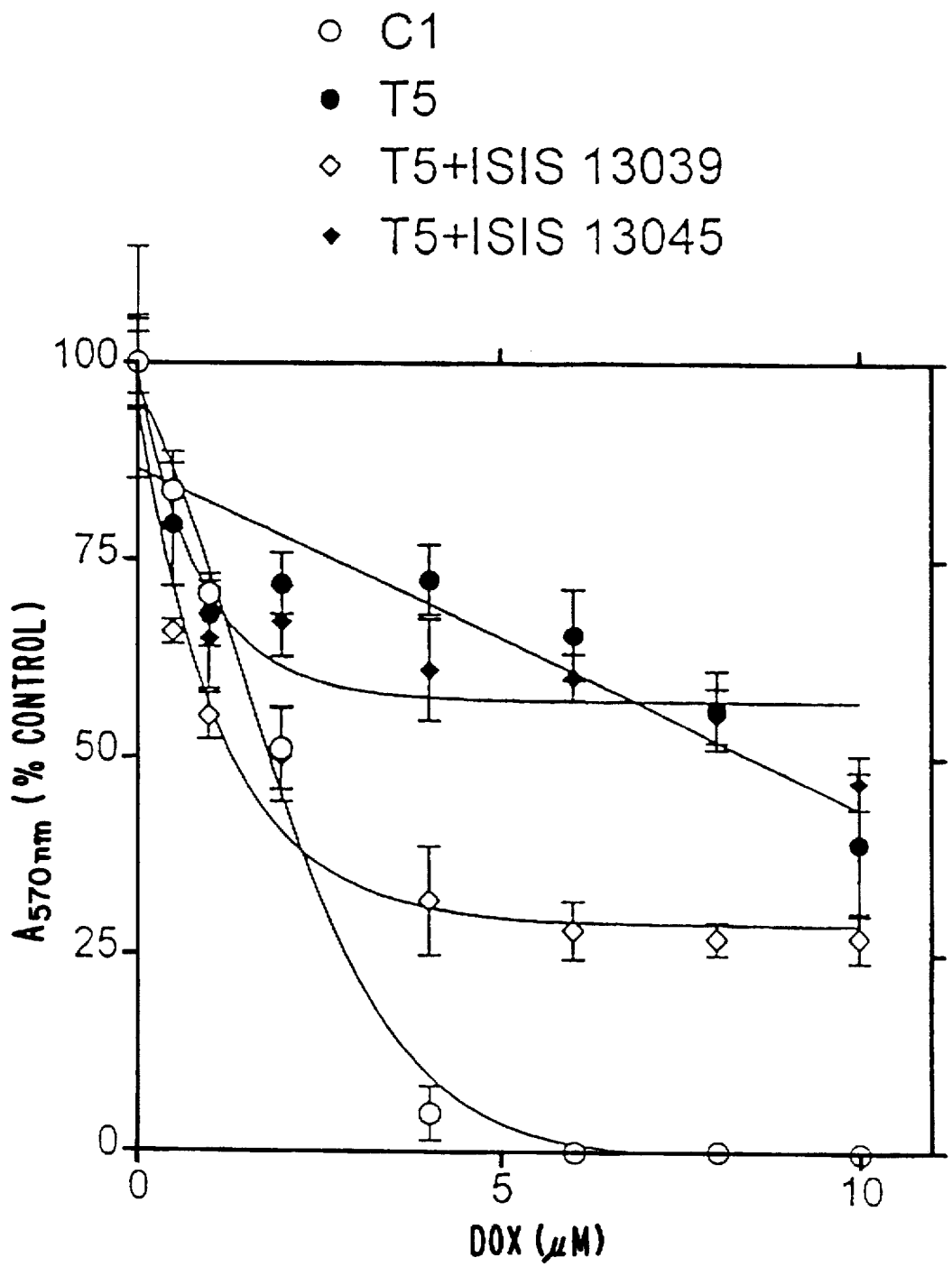

Treatment with the antisense oligonucleotide ISIS 13041 (PS backbone, 8-deoxy gap) gave a virtually complete reversal of resistance to vincristine and over 50% reversal of resistance to doxorubicin (FIG. 2). This oligonucleotide compound is, therefore, highly preferred. ISIS 13039 (PS backbone, 12-deoxy gap) gave approximately 70% reversal of resistance to vincristine and 30% reversal of resistance to doxorubicin (FIG. 4). This compound is also highly preferred. ISIS 13038 (12-deoxy gap, mixed PS/PO backbone) gave approximately 40% reversal of resistance to vincristine, substantially more than control oligonucleotide 13044, but was very similar to control when tested with doxorubicin (FIG. 3). ISIS 13038 is preferred. ISIS 13040 (8-deoxy gap, PS/PO backbone) gave approximately 45% reversal of resistance to vincristine and doxorubicin, (FIG. 1), but the control, ISIS 13043, also gave partial reversal.

Reduction in MRP protein levels after double dose of oligo

Figure 5A:
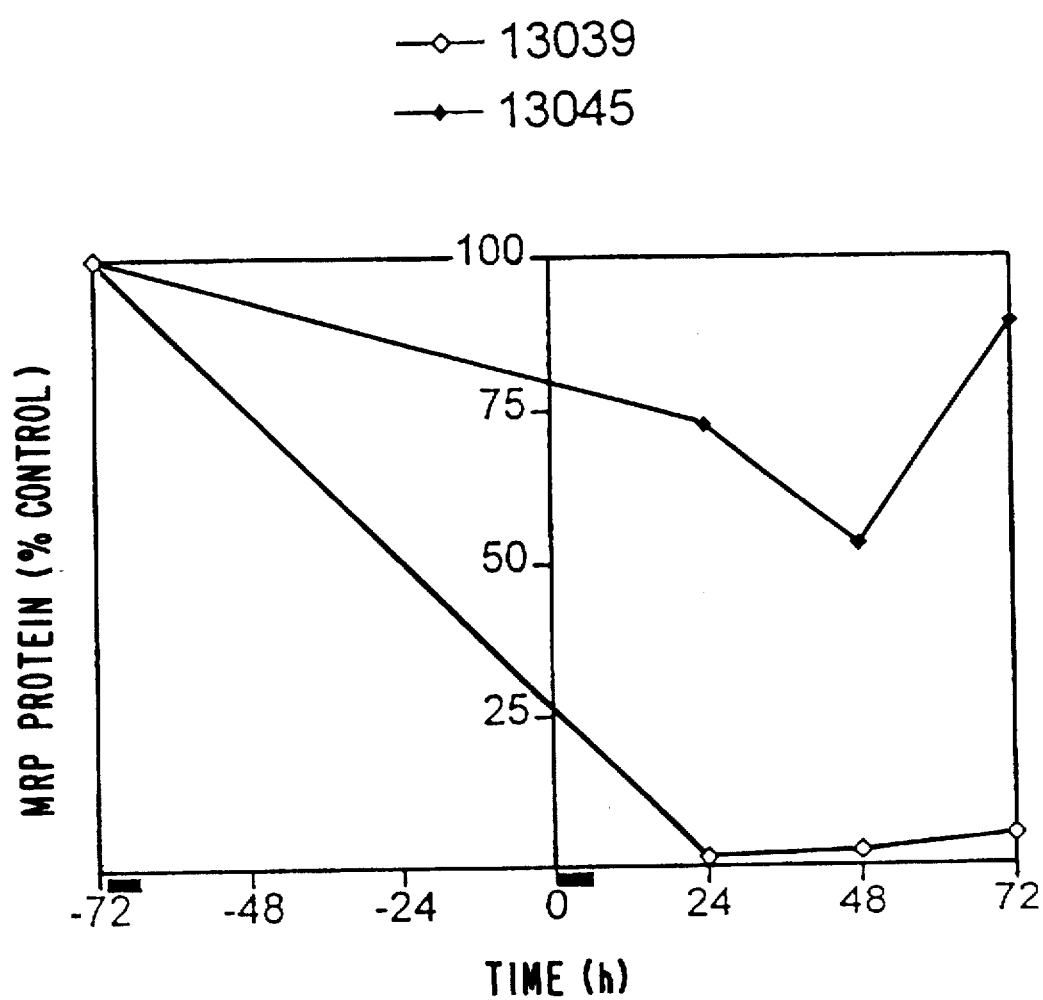
FIG. 5a shows the results of treatment with ISIS 13039 (open diamonds) or its scrambled control, ISIS 13045 (closed diamonds).
Figure 5B:
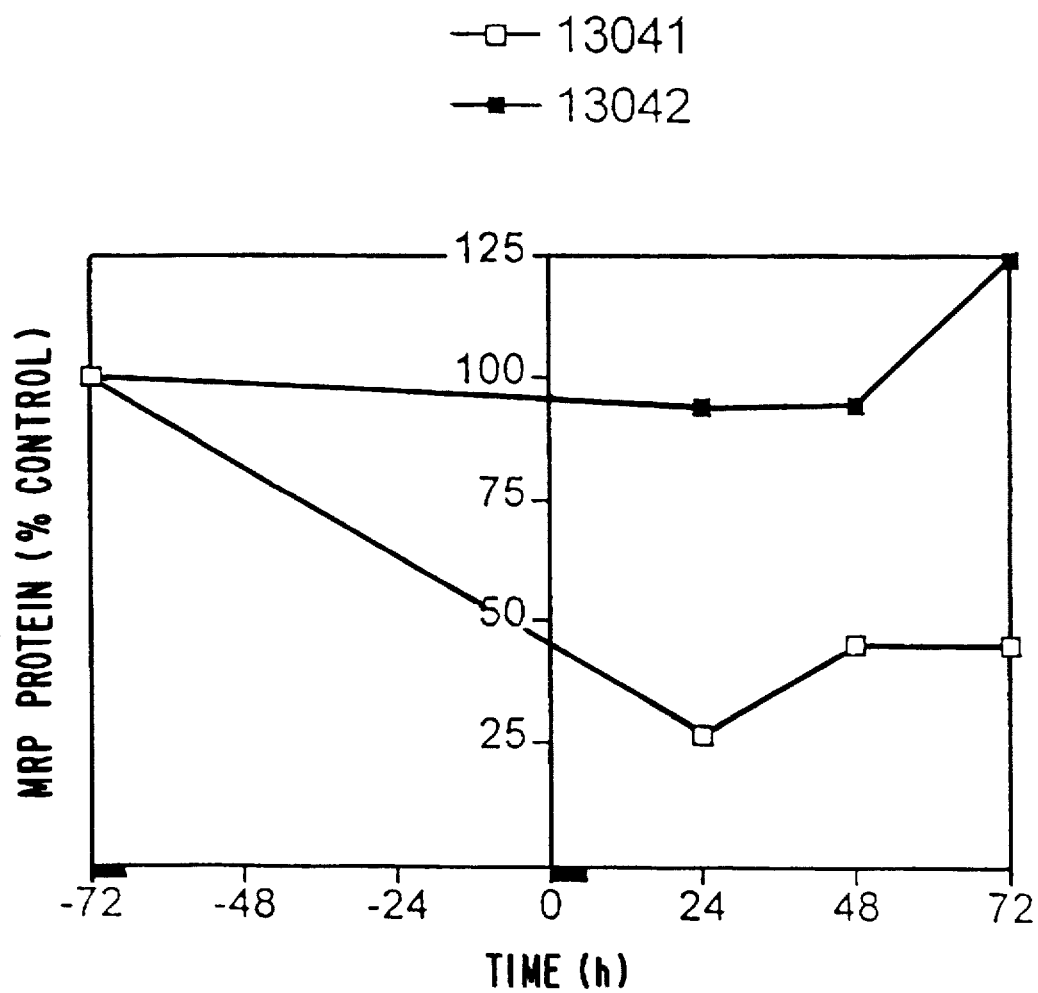
FIG. 5b shows the results of treatment with ISIS 13041 (open squares) or its scrambled control, ISIS 13042 (closed squares).

Levels of MRP protein were assayed by immunoblot analysis after cells were treated with two doses of oligonucleotide. As shown in FIG. 5, MRP levels were reduced and held at low levels for at least 72 hours when treated with ISIS 13039 or ISIS 13041.

Antisense inhibition of H69AR tumor xenografts in nude mice

Figure 6:
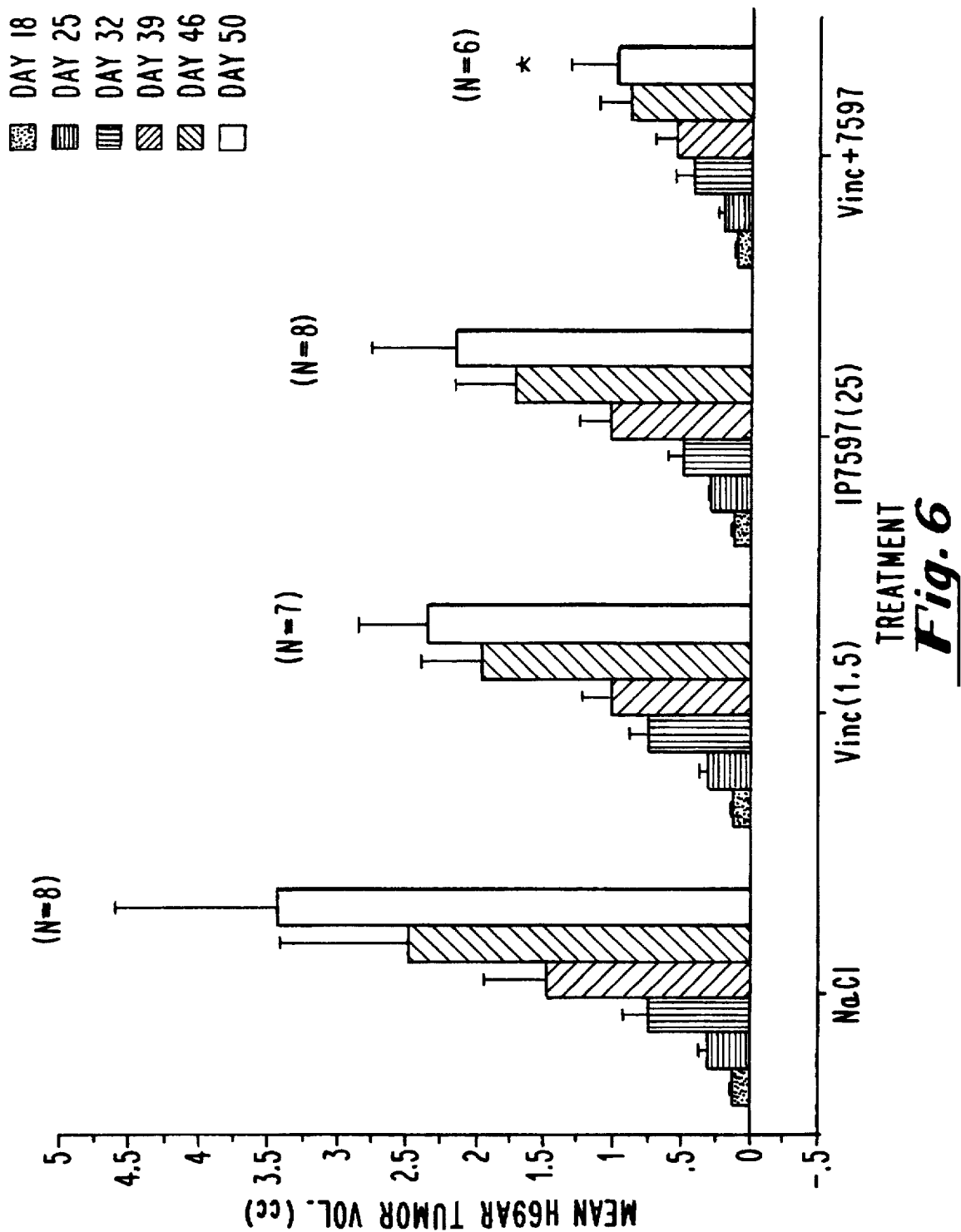
FIG. 6 is a bar graph showing inhibition of H69AR tumor growth in nude mice at six time points after treatment with ISIS 7597 (IP7597), vincristine (Vinc), ISIS 7597 plus vincristine (Vinc+7597) or saline control (NaCl).

The effect of ISIS 7597 on growth of H69AR tumor xenografts in nude mice was examined both in comparison to and in combination with vincristine. Mice were implanted with tumor fragments and treated with ISIS 7597 (SEQ ID NO: 8, P=S, 25 mg/kg), vincristine, ISIS 7597 plus vincristine, or saline (control). Tumor size was measured weekly and the results are shown in FIG. 6. ISIS 7597 inhibited tumor growth by 30% on day 46 and by 38% on day 50. This was better than vincristine alone (22% and 31% on days 46 and 50, respectively). The combination of ISIS 7597 and vincristine gave the greatest inhibition (63% and 70% on days 46 and 50, respectively).

Several preferred embodiments of this invention are exemplified in accordance with the following nonlimiting examples.

EXAMPLES

Example 1

Synthesis and characterization of oligonucleotides

Unmodified DNA oligonucleotides were synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2M solution of 3H-1,2-benzodithiole-3-one 1,1-dioxide in acetonitrile for the stepwise thiation of the phosphite linkages. The thiation cycle wait step was increased to 68 seconds and was followed by the capping step.

2'-O-methyl phosphorothioate oligonucleotides were synthesized using 2'-O-methyl β-cyanoethyldiisopropyl-phosphoramidites (Chemgenes, Needham Mass.) and the standard cycle for unmodified oligonucleotides, except the wait step after pulse delivery of tetrazole and base was increased to 360 seconds. The 3'-base used to start the synthesis was a 2'-deoxyribonucleotide. 2'-O-propyl oligonucleotides were prepared by a slight modification of this procedure.

2'-Fluoro phosphorothioate oligonucleotides were synthesized using 5'-dimethoxytrityl-3'-phosphoramidites and prepared as disclosed in U.S. patent application Ser. No. 463,358, filed Jan. 11, 1990, and 566,977, filed Aug. 13, 1990, which are assigned to the same assignee as the instant application and which are incorporated by reference herein. The 2'-fluoro oligonucleotides were prepared using phosphoramidite chemistry and a slight modification of the standard DNA synthesis protocol: deprotection was effected using methanolic ammonia at room temperature.

2'-(2-methoxyethyl)-modified amidites are synthesized according to Martin, P., *Helv. Chim. Acta* 1995, 78,486–504. For ease of synthesis, the last nucleotide was a deoxynucleotide. In most cases, 2'-O-CH$_2$CH$_2$OCH$_3$-cytosines were 5-methyl cytosines.

Synthesis of 5-Methyl cytosine monomers 2,2'-Anhydro [1-(β-D-arabinofuranosyl)-5-methyluridine]

5-Methyluridine (ribosylthymine, commercially available through Yamasa, Choshi, Japan) (72.0 g, 0.279M), diphenylcarbonate (90.0 g, 0.420M) and sodium bicarbonate (2.0 g, 0.024M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5L), with stirring. The product formed a gum. The ether was decanted and the residue was dissolved in a minimum amount of methanol (ca. 400 mL). The solution was poured into fresh ether (2.5L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2'-O-Methoxyethyl-5-methyluridine 2,2'-Anhydro-5-methyluridine (195 g, 0.81M), tris(2-methoxyethyl)borate (231 g, 0.98M) and 2-methoxyethanol (1.2L) were added to a 2L stainless steel pressure vessel and placed in a pre-heated oil bath at 160° C. After heating for 48 hours at 155°–160° C., the vessel was opened and the solution evaporated to dryness and triturated with MeOH (200 mL). The residue was suspended in hot acetone (1L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine

2'-O-Methoxyethyl-5-methyluridine (160 g, 0.506M) was co-evaporated with pyridine (250 mL) and the dried residue dissolved in pyridine (1.3L). A first aliquot of dimethoxytrityl chloride (94.3 g, 0.278M) was added and the mixture stirred at room temperature for one hour. A second aliquot of dimethoxytrityl chloride (94.3 g, 0.278M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167M), DMF/pyridine (750 mL of a 3:1 mixture prepared from 562 mL of DMF and 188 mL of pyridine) and acetic anhydride (24.38 mL, 0.258M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/Hexane (4:1). Pure product fractions were evaporated to yield 96 g (84%).

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144M) in $CH_3CN$ (700 mL) and set aside. Triethylamine (189 mL, 1.44M) was added to a solution of triazole (90 g, 1.3M) in $CH_3CN$ (1L), cooled to −5° C. and stirred for 0.5 h using an overhead stirrer. $POCl_3$ was added dropwise, over a 30 minute period, to the stirred solution maintained at 0°–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

$N^4$-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134M) was dissolved in DMF (800 mL) and benzoic anhydride (37.2 g, 0.165M) was added with stirring. After stirring for 3 hours, tlc showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/Hexane (1:1) containing 0.5% $Et_3NH$ as the eluting solvent. The pure product fractions were evaporated to give 90 g (90%) of the title compound.

$N^4$-Benzoyl-2'-O-methoxyethyl-5'-O-dimethoxytrityl-5-methylcytidine-3'-amidite $N^4$-Benzoyl-2'-O-methoxyethyl-5'-O-dimethoxytrityl-5-methylcytidine (74 g, 0.10M) was dissolved in $CH_2Cl_2$ (1L). Tetrazole diisopropylamine (7.1 g) and 2-cyanoethoxy-tetra-(isopropyl)phosphite (40.5 mL, 0.123M) were added with stirring, under a nitrogen atmosphere. The resulting mixture was stirred for 20 hours at room temperature (tlc showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL) and the extracts were combined, dried over $MgSO_4$ and concentrated. The residue obtained was chromatographed on a 1.5 kg silica column using EtOAc\Hexane (3:1) as the eluting solvent. The pure fractions were combined to give 90.6 g (87%) of the title compound.

2'-O-hexylaminocholesterol nucleosides were synthesized and incorporated into oligonucleotides according to Manoharan et al. *Tetrahedron Lett.* 1995, 36, 3651–3654.

After cleavage from the controlled pore glass column (Applied Biosystems) and deblocking in concentrated ammonium hydroxide at 55° C. for 18 hours, the oligonucleotides were purified by precipitation twice out of 0.5M NaCl with 2.5 volumes ethanol. Analytical gel electrophoresis was accomplished in 20% acrylamide, 8M urea, 45 mM Tris-borate buffer, pH 7.0. Oligodeoxynucleotides and phosphorothioate oligonucleotides were judged from electrophoresis to be greater than 80% full length material.

The relative amounts of phosphorothioate and phosphodiester linkages obtained by this synthesis were periodically checked by $^{31}$P NMR spectroscopy. The spectra were obtained at ambient temperature using deuterium oxide or dimethyl sulfoxide-$d_6$ as solvent. Phosphorothioate samples typically contained less than one percent of phosphodiester linkages.

Example 2

Selection and maintenance of multidrug resistant cell line H69AR cells

H69AR, a doxorubicin-resistant human small cell lung carcinoma cell line, was selected and maintained as described in Mirski et al. Cancer Res. 1987, 47, 2594–2598.

Example 3

Lipofection and oligonucleotide treatment of H69AR cells for analysis by whole cell ELISA $1.5 \times 10^6$ cells were plated into 35 mm tissue culture wells and allowed to attach overnight. The cells were then washed twice with 3 ml of serum-free medium prior to lipofection. Oligonucleotides were added to a concentration of 0.3 µM in 1 ml of serum-free medium in a polystyrene tube. 10 µl of LIPOFECTIN™ (GIBCO-BRL) was then added and the mixture was vortexed. After ten minutes at room temperature, the DNA/LIPOFECTIN™ suspension was added to the cells and incubated for four hours at 37° C. After this incubation, 1 ml of 20% Hyclone serum in RPMI was added and left at 37° C. overnight. The next day the suspension was removed and replaced with fresh medium. On the following day, the lipofection was repeated as before and the cells were harvested 48 hours after the second lipofection.

Example 4

Whole Cell ELISA of H69AR Cells after Oligonucleotide Treatment

Cells were harvested, counted and washed twice with PBS. Cells were resuspended at $0.5-1 \times 10^5$ cells/ml in PBS and 100 µl was plated in each well of an ELISA plate. Plates were dried overnight at 37° and autocrosslinked twice in a Stratalinker (Stratagene, La Jolla, Calif.). Plates were rehydrated in TBST, 200 µl/well for 2×5 minutes. Wells were blocked for 1.5–2 hours at room temperature with 200 µl TBST containing 5% NGS, 1% BSA. Primary antibody [50 µl of monoclonal antibody 3.186; Mirski et al. Cancer Res. 1989, 49, 5719–5724] diluted in blocking solution was added and plates were incubated for 1.5–2 hours in a humidified chamber at room temperature. Plates were washed 3×5 minutes with 200 µl TBST. Plates were incubated with 50 µl secondary antibody diluted in blocking solution for 1–1.5 hours at room temperature in a humidified chamber. Plates were washed for with 200 µl TBST, 3×5 minutes. Color detection was by horseradish peroxidase [incubated with 100 µl OPD/$H_2O_2$/citrate buffer (250 µl 10 mg/ml OPD in methanol/25 µl 3% $H_2O_2$/24.8 ml 0.05M citrate pH 5)] in the dark for 30 minutes at room temperature, stop reaction with 25 µl 8N $H_2SO_4$, and read absorbance at 490 nm] or by alkaline phosphatase [incubate with 50 µl substrate solution (1 PNPP tablet in 5 ml 50 mM $NaHCO_3$, pH 9.6, 1 mM $MgCl_2$) for 30 minutes in humid chamber at room temperature, stop reaction with 50 µl 0.4M NaOH, read absorbance at 405 nm].

Example 5

RNA Analysis of H69AR Cells Treated with Antisense Oligonucleotides Specifically Hybridizable with MRP $10 \times 10^6$ cells were plated per T75 flask and allowed to attach overnight. Cells were washed twice with serum-free medium before incubation with 6 ml of oligonucleotide/LIPOFECTIN™ suspension (0.3 µM oligonucleotide; 10 µl LIPOFECTIN™ per ml of serum-free medium) at 37° C. for 4 hours after which 6 ml of 20% Hyclone serum in RPMI was added and left overnight. Fresh medium was added the next day. On the following day polyadenylated RNA was isolated using a MICRO-FASTTRACK mRNA isolation kit (InVitrogen). The RNA was then separated by electrophoresis on a formaldehyde-agarose denaturing gel and then transferred to a nylon membrane (Zetaprobe, Biorad). The membrane was prehybridized in 50% formamide, 5×SSC, 5×Denhardt's solution, 1% SDS and 100 µg/ml sheared, denatured herring testis DNA for 4 hours at 42° C. The membrane was then hybridized overnight at 42° C. with a 2.0 kb cDNA fragment of MRP labelled with [$\alpha$-$^{32}$P]dCTP using a random prime kit (GIBCO/BRL). The blot was washed three times in 0.1% SDS and 0.1×SSC for 20 minutes at 52° C. and autoradiographed. Only in overloaded lanes was any RNA detectable as a faint band after oligonucleotide treatment with ISIS 7597 and 7598.

Example 6

Diagnostic assay for MRP-associated tumors using xenografts in nude mice

Tumors arising from MRP overexpression are diagnosed and distinguished from other tumors using this assay. A biopsy sample of the tumor is treated, e.g., with collagenase or trypsin or other standard methods, to dissociate the tumor mass. $5 \times 10^6$ tumor cells are implanted in the inner thighs of two or more nude mice. Antisense oligonucleotide suspended in saline is administered to one or more mice by intraperitoneal injection three times weekly beginning on day 4 after tumor cell inoculation. Saline only is given to a control mouse. Oligonucleotide dosage is 25 mg/kg. Tumor size is measured and tumor volume is calculated on the eleventh treatment day. Tumor volume of the oligonucleotide-treated mice is compared to that of the control mouse. The volume of MRP-associated tumors in the treated mice are measurably smaller than tumors in the control mouse. Tumors arising from causes other than MRP overexpression are not expected to respond to the oligonucleotides targeted to the nucleic acids encoding MRP and, therefore, the tumor volumes of oligonucleotide-treated and control mice are equivalent.

Example 7

Detection of MRP overexpression

Oligonucleotides are radiolabeled after synthesis by $^{32}$P labeling at the 5' end with polynucleotide kinase. Sambrook et al., "Molecular Cloning, A Laboratory Manual," Cold Spring Harbor Laboratory Press, 1989, Volume 2, pg. 11.31–11.32. Radiolabeled oligonucleotide is contacted with tissue or cell samples suspected of MRP overexpression, such as tumor biopsy samples, under conditions in which specific hybridization can occur, and the sample is washed to remove unbound oligonucleotide. A similar control is maintained wherein the radiolabeled oligonucleotide is contacted with normal cell or tissue sample under conditions that allow specific hybridization, and the sample is washed to remove unbound oligonucleotide. Radioactivity remaining in the sample indicates bound oligonucleotide and is quantitated using a scintillation counter or other routine means. Comparison of the radioactivity remaining in the samples from normal and tumor cells indicates overexpression of MRP.

Radiolabeled oligonucleotides of the invention are also useful in autoradiography. Tissue sections are treated with radiolabeled oligonucleotide and washed as described above, then exposed to photographic emulsion according to standard autoradiography procedures. A control with normal cell or tissue sample is also maintained. The emulsion, when developed, yields an image of silver grains over the regions expressing MRP, which is quantitated. The extent of MRP overexpression is determined by comparison of the silver grains observed with normal and tumor cells.

Analogous assays for fluorescent detection of MRP overexpression use oligonucleotides of the invention which are labeled with fluorescein or other fluorescent tags. Labeled DNA oligonucleotides are synthesized on an automated DNA synthesizer (Applied Biosystems model 380B) using standard phosphoramidite chemistry with oxidation by iodine. β-cyanoethyldiisopropyl phosphoramidites are purchased from Applied Biosystems (Foster City, Calif.). Fluorescein-labeled amidites are purchased from Glen Research (Sterling, Va.). Incubation of oligonucleotide and biological sample is carried out as described for radiolabeled oligonucleotides except that instead of a scintillation counter, a fluorescence microscope is used to detect the fluorescence. Comparison of the fluorescence observed in samples from normal and tumor cells indicates MRP overexpression.

Example 8

HeLa cell culture and oligonucleotide treatment

T5 and C1 HeLa cells were obtained and maintained as described in Canitrot et al. *Anti-Cancer Drugs* 1996, 7(suppl. 3), 93–99. Cells were treated with oligonucleotide in LIPOFECTIN™ essentially as described by Canitrot et al., except that a double treatment was used in some cases. For double treatment, cells were treated with oligonucleotide (500 nM) on day 1 and day 4 after plating. On day 5, cells were harvested for RNA and/or protein isolation. For MTT assay, chemotherapeutic agent was added on day 5 and the assay was performed on day 8.

Example 9

Measurement of MRP mRNA in HeLa cells

RNA quantitation was done by Northern blot analysis according to Canitrot et al., supra.

Example 10

Measurement of MRP protein in HeLa cells

Protein quantitation was done by immunoblot analysis according to Canitrot et al., supra.

Example 11

Chemosensitivity testing in HeLa cells

Drug sensitivity of transfected HeLa cells was measured using a 3-[4,5-dimethylthiazol-2-yl]-2,5-diphenyltetrazolium bromide (MTT) -based cytotoxicity assay essentially as described in Cole et al. *Cancer Chemother. Pharmacol.* 1986, 17, 259–263 and Canitrot et al. *Anti-Cancer Drugs* 1996, 7(suppl. 3), 93–99]. The MTT assay was performed 72 hours after chemotherapeutic agent was added to the cells.

Example 12

H69AR tumor xenograft studies

H69AR tumor fragments (approximately 25 mg each) were taken from two eighth-generation fragment xenografts in nude mice and implanted into recipient mice for study. Eighteen days later the animals were separated into three groups (7 or 8 mice per group) for treatment with either saline, vincristine, ISIS 7597 (SEQ ID NO: 8, P=S) or vincristine plus ISIS 7597. Treatment was 10 ml/kg daily for saline. For vincristine, three 1.5 mg/kg doses were given intraperitoneally on days 22, 36 and 46 for both the vincristine and vincristine+oligonucleotide groups. ISIS 7597 (25 mg/kg) was given daily by intravenous or intraperitoneal injection, beginning on day 19, for both the oligonucleotide and vincristine+oligonucleotide groups. Tumor size was measured weekly using calipers and converted to volume (cc), using the formula [Volume=Length×Width$^2$/2]. Animal weights were also measured weekly. Treatment was terminated and animals sacrificed on day 50.

What is claimed is:

1. An oligonucleotide comprising 8 to 30 nucleotides specifically hybridizable with a nucleic acid encoding multidrug resistance-associated protein and capable of inhibiting the expression of multidrug resistance-associated protein.

2. The oligonucleotide of claim 1 which is specifically hybridizable with mRNA encoding multidrug resistance-associated protein.

3. The oligonucleotide of claim 1 which specifically hybridizes with DNA encoding multidrug resistance-associated protein to form a triple stranded structure.

4. The oligonucleotide of claim 2 specifically hybridizable with a transcription initiation site, a translation initiation site, 5'-untranslated sequence, 3' untranslated sequence, coding sequence or an intron/exon junction of an mRNA encoding multidrug resistance-associated protein.

5. A pharmaceutical composition comprising an oligonucleotide of claim 1 and a pharmaceutically acceptable carrier.

6. The oligonucleotide of claim 1 wherein at least one of the intersugar linkages between nucleotides of the oligonucleotide is a phosphorothioate linkage.

7. The oligonucleotide of claim 1 wherein at least one of the nucleotides is modified at the 2' position.

8. The oligonucleotide of claim 7 wherein the nucleotide modification is 2'-O-methyl, 2'-O-propyl, 2'-methoxyethoxy or 2'-fluoro.

9. The oligonucleotide of claim 8 which is a chimeric oligonucleotide.

10. The oligonucleotide of claim 9 which is a gapped oligonucleotide.

11. The oligonucleotide of claim 1 comprising SEQ ID NO: 17, 18, 19, 20, 21, 22, 23, 24, 25, 26, 27 or 28.

12. An oligonucleotide comprising 8 to 30 nucleotides specifically hybridizable with a nucleic acid encoding multidrug resistance-associated protein and capable of inhibiting the expression of multidrug resistance-associated protein, wherein said oligonucleotide comprises at least one 2'-methoxyethoxy modification.

13. The oligonucleotide of claim 12 which is a chimeric oligonucleotide.

14. The oligonucleotide of claim 13 which is a gapped oligonucleotide.

15. An oligonucleotide of claim 12 specifically hybridizable with a transcription initiation site, a translation initiation site, 5'-untranslated sequence, 3' untranslated sequence, coding sequence or an intron/exon junction of an mRNA encoding multidrug resistance-associated protein.

16. A pharmaceutical composition comprising an oligonucleotide of claim 12 and a pharmaceutically acceptable carrier.

17. An oligonucleotide of claim 12 wherein at least one of the intersugar linkages between nucleotides of the oligonucleotide is a phosphorothioate linkage.

18. An oligonucleotide of claim 12 comprising SEQ ID NO: 2, 3, 4, 5, 6, 7, 8, 9, 10, 11, 12, 13, 14, 15, 16, 17, 18, 19, 20, 21, 22, 23, 24, 25, 26, 27 or 28.

19. An oligonucleotide comprising SEQ ID NO: 8 and at least one 2' methoxyethoxy modification.

20. The oligonucleotide of claim 19 which is a chimeric oligonucleotide.

21. The oligonucleotide of claim 20 which is a gapped oligonucleotide.

22. A method of inhibiting the synthesis of multidrug resistance-associated protein in a cell or tissue comprising contacting a cell or tissue with an oligonucleotide comprising 8 to 30 nucleotides specifically hybridizable with a nucleic acid encoding multidrug resistance-associated protein and capable of modulating the expression of multidrug resistance-associated protein.

23. A method of inhibiting the synthesis of multidrug resistance-associated protein in a cell or tissue comprising contacting a cell or tissue with an oligonucleotide comprising an oligonucleotide comprising SEQ ID NO: 8 and at least one 2' methoxyethoxy modification.

24. The method of claim 23 wherein the oligonucleotide is a chimeric oligonucleotide.

25. The method of claim 23 wherein the oligonucleotide is a gapped oligonucleotide.

26. A method of treating an animal suspected of having a condition which is characterized by overexpression of multidrug resistance-associated protein comprising administering to said animal a therapeutically effective amount of an oligonucleotide having 8 to 30 nucleotides specifically hybridizable with a nucleic acid encoding multidrug resistance-associated protein and capable of inhibiting the expression of multidrug resistance-associated protein.

27. The method of claim 26 wherein the oligonucleotide is administered in conjunction with a chemotherapeutic drug treatment for cancer.

28. The method of claim 27 wherein the condition is a multidrug-resistant cancer.

29. The method of claim 27 wherein the multidrug-resistant cancer is small-cell lung cancer.

30. A method for improving the efficacy of a chemotherapeutic drug treatment of a disease, said method comprising administering in conjunction with a chemotherapeutic drug treatment an oligonucleotide comprising 8 to 30 nucleotides specifically hybridizable with a nucleic acid encoding multidrug resistance-associated protein and capable of inhibiting the expression of multidrug resistance-associated protein.

31. The method of claim 30 wherein the disease is cancer.

32. A method for preventing the development of multidrug resistance during a chemotherapeutic drug treatment of a disease, said method comprising administering in conjunction with a chemotherapeutic drug treatment an oligonucleotide comprising 8 to 30 nucleotides specifically hybridizable with a nucleic acid encoding multidrug resistance-associated protein and capable of inhibiting the expression of multidrug resistance-associated protein.

33. The method of claim 32 wherein the disease is cancer.

34. A method of treating an animal suspected of having a condition which is characterized by leukotriene production comprising administering to said animal a therapeutically effective amount of an oligonucleotide having 8 to 30 nucleotides specifically hybridizable with a nucleic acid encoding multidrug resistance-associated protein and capable of inhibiting the expression of multidrug resistance-associated protein.

35. The method of claim 34 wherein the condition is an inflammatory condition.

* * * * *

UNITED STATES PATENT AND TRADEMARK OFFICE
CERTIFICATE OF CORRECTION

PATENT NO. : 5,801,154
DATED : September 1, 1998
INVENTOR(S) : Baracchini, et al.

It is certified that error appears in the above-indentified patent and that said Letters Patent is hereby corrected as shown below:

On the title page, item [57],

ABSTRACT, at line 5, delete "referred and insert --preferred--.

Signed and Sealed this

Nineteenth Day of January, 1999

Attest:

*Acting Commissioner of Patents and Trademarks*

*Attesting Officer*

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 1:

CGGGGCCGCA ACGCCGCCUG                          2 0

( 2 ) INFORMATION FOR SEQ ID NO:2:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 2:

CGGGGCCGCA ACGCCGCCTG                                                                           20

( 2 ) INFORMATION FOR SEQ ID NO:3:

( i ) SEQUENCE CHARACTERISTICS:
                    ( A ) LENGTH: 20
                    ( B ) TYPE: Nucleic Acid
                    ( C ) STRANDEDNESS: Single
                    ( D ) TOPOLOGY: Linear ( i v ) ANTI-SENSE: Yes ( x i ) SEQUENCE DESCRIPTION: SEQ ID NO: 3:

GGTGATCGGG CCCGGTTGCT                                                                           20

( 2 ) INFORMATION FOR SEQ ID NO: 4:

( i ) SEQUENCE CHARACTERISTICS:
                    ( A ) LENGTH: 20
                    ( B ) TYPE: Nucleic Acid
                    ( C ) STRANDEDNESS: Single
                    ( D ) TOPOLOGY: Linear ( i v ) ANTI-SENSE: Yes ( x i ) SEQUENCE DESCRIPTION: SEQ ID NO: 4:

CCGGTGGCGC GGGCGGCGGC                                                                           20

( 2 ) INFORMATION FOR SEQ ID NO: 5:

( i ) SEQUENCE CHARACTERISTICS:
                    ( A ) LENGTH: 20
                    ( B ) TYPE: Nucleic Acid
                    ( C ) STRANDEDNESS: Single
                    ( D ) TOPOLOGY: Linear ( i v ) ANTI-SENSE: Yes ( x i ) SEQUENCE DESCRIPTION: SEQ ID NO: 5:

AGCCCCGGAG CGCCATGCCG                                                                           20

( 2 ) INFORMATION FOR SEQ ID NO: 6:

( i ) SEQUENCE CHARACTERISTICS:
                    ( A ) LENGTH: 20
                    ( B ) TYPE: Nucleic Acid
                    ( C ) STRANDEDNESS: Single
                    ( D ) TOPOLOGY: Linear ( i v ) ANTI-SENSE: Yes ( x i ) SEQUENCE DESCRIPTION: SEQ ID NO: 6:

TCGGAGCCAT CGGCGCTGCA                                                                           20

( 2 ) INFORMATION FOR SEQ ID NO: 7:

( i ) SEQUENCE CHARACTERISTICS:
                    ( A ) LENGTH: 20
                    ( B ) TYPE: Nucleic Acid
                    ( C ) STRANDEDNESS: Single
                    ( D ) TOPOLOGY: Linear ( i v ) ANTI-SENSE: Yes ( x i ) SEQUENCE DESCRIPTION: SEQ ID NO: 7:

GGCACCCACA CGAGGACCGT                                                                           20

( 2 ) INFORMATION FOR SEQ ID NO: 8:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 8:

TGCTGTTCGT GCCCCCGCCG                                                                    20

( 2 ) INFORMATION FOR SEQ ID NO: 9:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 9:

CGCGCTGCTT CTGGCCCCA                                                                     20

( 2 ) INFORMATION FOR SEQ ID NO: 10:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 10:

GCGGCGATGG GCGTGGCCAG                                                                    20

( 2 ) INFORMATION FOR SEQ ID NO: 11:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 11:

CAGGAGGTCC GATGGGGCGC                                                                    20

( 2 ) INFORMATION FOR SEQ ID NO: 12:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 12:

GCTCACACCA AGCCGGCGTC                                                                    20

( 2 ) INFORMATION FOR SEQ ID NO: 13:

( i ) SEQUENCE CHARACTERISTICS:

(A) LENGTH: 20
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 13:

AGGCCCTGCA GTTCTGACCA                                                                20

(2) INFORMATION FOR SEQ ID NO: 14:

(i) SEQUENCE CHARACTERISTICS:
    (A) LENGTH: 20
    (B) TYPE: Nucleic Acid
    (C) STRANDEDNESS: Single
    (D) TOPOLOGY: Linear (iv) ANTI-SENSE: Yes (xi) SEQUENCE DESCRIPTION: SEQ ID NO: 14:

CTCCTCCCTG GGCGCTGGCA                                                                20

(2) INFORMATION FOR SEQ ID NO: 15:

(i) SEQUENCE CHARACTERISTICS:
    (A) LENGTH: 20
    (B) TYPE: Nucleic Acid
    (C) STRANDEDNESS: Single
    (D) TOPOLOGY: Linear (iv) ANTI-SENSE: Yes (xi) SEQUENCE DESCRIPTION: SEQ ID NO: 15:

ACCGGATGGC GGTGGCTGCT                                                                20

(2) INFORMATION FOR SEQ ID NO: 16:

(i) SEQUENCE CHARACTERISTICS:
    (A) LENGTH: 20
    (B) TYPE: Nucleic Acid
    (C) STRANDEDNESS: Single
    (D) TOPOLOGY: Linear (iv) ANTI-SENSE: Yes (xi) SEQUENCE DESCRIPTION: SEQ ID NO: 16:

CGCATCTCTG TCTCTCCTGG                                                                20

(2) INFORMATION FOR SEQ ID NO: 17:

(i) SEQUENCE CHARACTERISTICS:
    (A) LENGTH: 20
    (B) TYPE: Nucleic Acid
    (C) STRANDEDNESS: Single
    (D) TOPOLOGY: Linear (iv) ANTI-SENSE: Yes (xi) SEQUENCE DESCRIPTION: SEQ ID NO: 17:

CAGAAGCCCC GGAGCGCCAT                                                                20

(2) INFORMATION FOR SEQ ID NO: 18:

(i) SEQUENCE CHARACTERISTICS:
    (A) LENGTH: 20
    (B) TYPE: Nucleic Acid
    (C) STRANDEDNESS: Single
    (D) TOPOLOGY: Linear ( i v ) ANTI-SENSE: Yes ( x i ) SEQUENCE DESCRIPTION: SEQ ID NO: 18:

GCCCCCGCCG TCTTTGACAG                                                                                          20

( 2 ) INFORMATION FOR SEQ ID NO: 19:

( i ) SEQUENCE CHARACTERISTICS:
                ( A ) LENGTH: 20
                ( B ) TYPE: Nucleic Acid
                ( C ) STRANDEDNESS: Single
                ( D ) TOPOLOGY: Linear ( i v ) ANTI-SENSE: Yes ( x i ) SEQUENCE DESCRIPTION: SEQ ID NO: 19:

GTGATGCTGT TCGTGCCCCC                                                                                          20

( 2 ) INFORMATION FOR SEQ ID NO: 20:

( i ) SEQUENCE CHARACTERISTICS:
                ( A ) LENGTH: 20
                ( B ) TYPE: Nucleic Acid
                ( C ) STRANDEDNESS: Single
                ( D ) TOPOLOGY: Linear ( i v ) ANTI-SENSE: Yes ( x i ) SEQUENCE DESCRIPTION: SEQ ID NO: 20:

CTCACGGTGA TGCTGTTCGT                                                                                          20

( 2 ) INFORMATION FOR SEQ ID NO: 21:

( i ) SEQUENCE CHARACTERISTICS:
                ( A ) LENGTH: 20
                ( B ) TYPE: Nucleic Acid
                ( C ) STRANDEDNESS: Single
                ( D ) TOPOLOGY: Linear ( i v ) ANTI-SENSE: Yes ( x i ) SEQUENCE DESCRIPTION: SEQ ID NO: 21:

CCCCCAGACA GGTTCACGCC                                                                                          20

( 2 ) INFORMATION FOR SEQ ID NO: 22:

( i ) SEQUENCE CHARACTERISTICS:
                ( A ) LENGTH: 20
                ( B ) TYPE: Nucleic Acid
                ( C ) STRANDEDNESS: Single
                ( D ) TOPOLOGY: Linear ( i v ) ANTI-SENSE: Yes ( x i ) SEQUENCE DESCRIPTION: SEQ ID NO: 22:

CTGGCCCCCA GACAGGTTCA                                                                                          20

( 2 ) INFORMATION FOR SEQ ID NO: 23:

( i ) SEQUENCE CHARACTERISTICS:
                ( A ) LENGTH: 20
                ( B ) TYPE: Nucleic Acid
                ( C ) STRANDEDNESS: Single
                ( D ) TOPOLOGY: Linear ( i v ) ANTI-SENSE: Yes ( x i ) SEQUENCE DESCRIPTION: SEQ ID NO: 23:

GCCAGGCTCA CGCGCTGCTT                                                                                          20

( 2 ) INFORMATION FOR SEQ ID NO: 24:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 24:

CACAGCCAGT TCCAGGCAGG 20

( 2 ) INFORMATION FOR SEQ ID NO: 25:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 25:

CCTGGGTCTT CACAGCCAGT 20

( 2 ) INFORMATION FOR SEQ ID NO: 26:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 26:

CGGCGGGGGC ACGAACAGCA 20

( 2 ) INFORMATION FOR SEQ ID NO: 27:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 27:

TCGTGGCCGC GTTCTCCCCG 20

( 2 ) INFORMATION FOR SEQ ID NO: 28:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 28:

CGTGTTGCTC GTGCCCGCCC 20